US008615295B2

(12) United States Patent
Savage et al.

(10) Patent No.: US 8,615,295 B2
(45) Date of Patent: Dec. 24, 2013

(54) EXTERNAL DEFIBRILLATOR

(75) Inventors: Walter T. Savage, Concord, CA (US); Shelley J. Savage, Concord, CA (US); Walter N. Maclay, Sunnyvale, CA (US); Douglas C. Morrison, Union City, CA (US); Thomas K. Geraty, San Jose, CA (US); Mark D. Brinkerhoff, San Jose, CA (US); Ronald S. Boeder, Livermore, CA (US); Tony M. Ton, San Diego, CA (US); Jeffrey S. Greger, Fairfield, CA (US)

(73) Assignee: Cardiothrive, Inc., Concord, CA (US)

( * ) Notice: Subject to any disclaimer, the term of this patent is extended or adjusted under 35 U.S.C. 154(b) by 586 days.

(21) Appl. No.: 12/724,269

(22) Filed: Mar. 15, 2010

(65) Prior Publication Data

US 2010/0241181 A1 Sep. 23, 2010

Related U.S. Application Data

(60) Provisional application No. 61/161,014, filed on Mar. 17, 2009.

(51) Int. Cl.
*A61N 1/39* (2006.01)

(52) U.S. Cl.
USPC .............................................................. 607/5

(58) Field of Classification Search
USPC .................................................. 607/4–5, 142
See application file for complete search history.

(56) References Cited

U.S. PATENT DOCUMENTS

| 5,240,995 A | 8/1993 | Gyory |
| 5,290,585 A | 3/1994 | Elton |
| 5,338,490 A | 8/1994 | Dietz |
| 5,362,420 A | 11/1994 | Itoh |
| 5,402,884 A | 4/1995 | Gilman et al. |
| 5,489,624 A | 2/1996 | Kantner |
| 5,536,768 A | 7/1996 | Kantner |
| 5,573,668 A | 11/1996 | Grosh |
| 5,643,252 A | 7/1997 | Waner et al. |
| 5,658,316 A | 8/1997 | Lamond et al. |
| 5,660,178 A | 8/1997 | Kantner |

(Continued)

FOREIGN PATENT DOCUMENTS

| DE | 10 2006 025864 | 12/2007 |
| EP | 1 834 622 | 9/2007 |
| WO | WO 03/020362 | 3/2003 |

OTHER PUBLICATIONS

PCT International Search Report of PCT/EP2007/009879; dated Apr. 29, 2008.
PCT International Preliminary Report on Patentability of PCT/US2010/027346; dated Sep. 20, 2011.
Extended European Search Report of EP 2408521; dated Jul. 10, 2012.

(Continued)

*Primary Examiner* — Amanda Patton
(74) *Attorney, Agent, or Firm* — DLA Piper LLP (US)

(57) ABSTRACT

A variety of arrangements and methods relating to a defibrillator are described. In one aspect of the invention, a defibrillator includes two paddles that each include a defibrillator electrode covered in a protective housing. The two paddles are sealed together using a releasable seal to form a paddle module such that the housings of the paddles form the exterior of the paddle module. An electrical system including at least a battery and a capacitor is electrically coupled with the paddles. The battery is arranged to charge the capacitor. The capacitor is arranged to apply a voltage at the defibrillator electrodes, which generates an electrical shock for arresting a cardiac arrhythmia.

44 Claims, 19 Drawing Sheets

(56) References Cited

U.S. PATENT DOCUMENTS

| | | | |
|---|---|---|---|
| 5,800,685 A | 9/1998 | Perrault | |
| 6,056,738 A | 5/2000 | Marchitto et al. | |
| 6,141,584 A | 10/2000 | Rockwell et al. | |
| 6,197,324 B1 | 3/2001 | Crittenden | |
| 6,251,100 B1 | 6/2001 | Flock et al. | |
| 6,266,563 B1 | 7/2001 | KenKnight et al. | |
| 6,315,722 B1 | 11/2001 | Yaegashi | |
| 6,329,488 B1 | 12/2001 | Terry | |
| 6,379,324 B1 | 4/2002 | Gartstein et al. | |
| 6,576,712 B2 | 6/2003 | Feldstein | |
| 6,596,401 B1 | 7/2003 | Terry | |
| 6,597,948 B1 | 7/2003 | Rockwell et al. | |
| 6,611,707 B1 | 8/2003 | Prausnitz | |
| 6,690,959 B2 | 2/2004 | Thompson | |
| 6,714,817 B2 * | 3/2004 | Daynes et al. | 607/5 |
| 6,797,276 B1 | 9/2004 | Glenn | |
| 6,803,420 B2 | 10/2004 | Cleary | |
| 6,908,453 B2 | 6/2005 | Fleming | |
| 6,908,681 B2 | 6/2005 | Terry | |
| 6,931,277 B1 | 8/2005 | Yuzhakov | |
| 7,072,712 B2 * | 7/2006 | Kroll et al. | 607/5 |
| 7,108,681 B2 | 9/2006 | Gartstein | |
| 7,226,439 B2 | 6/2007 | Pransnitz | |
| 7,463,917 B2 * | 12/2008 | Martinez | 600/395 |
| 7,645,263 B2 | 1/2010 | Angel et al. | |
| 7,797,044 B2 * | 9/2010 | Covey et al. | 607/5 |
| 8,024,037 B2 * | 9/2011 | Kumar | 607/5 |
| 2002/0082644 A1 | 6/2002 | Picardo et al. | |
| 2003/0017743 A1 | 1/2003 | Picardo et al. | |
| 2003/0055460 A1 | 3/2003 | Owen et al. | |
| 2003/0167075 A1 | 9/2003 | Fincke | |
| 2003/0197487 A1 | 10/2003 | Tamura et al. | |
| 2004/0105834 A1 | 6/2004 | Singh | |
| 2004/0143297 A1 | 7/2004 | Ramsey, III | |
| 2004/0166147 A1 | 8/2004 | Lundy | |
| 2004/0247655 A1 | 12/2004 | Asmus | |
| 2005/0123565 A1 | 6/2005 | Subramony | |
| 2006/0136000 A1 | 6/2006 | Bowers | |
| 2006/0142806 A1 | 6/2006 | Katzman et al. | |
| 2006/0206152 A1 | 9/2006 | Covey et al. | |
| 2007/0016268 A1 | 1/2007 | Carter et al. | |
| 2007/0078376 A1 | 4/2007 | Smith | |
| 2008/0097546 A1 | 4/2008 | Powers et al. | |
| 2010/0063559 A1 | 3/2010 | McIntyre et al. | |
| 2010/0160712 A1 | 6/2010 | Burnett et al. | |
| 2010/0241181 A1 | 9/2010 | Savage et al. | |

OTHER PUBLICATIONS

International Search Report dated Oct. 14, 2010 from International Application No. PCT/US2010/027346.
Written Opinion dated Oct. 14, 2010 from International Application No. PCT/US2010/027346.
Written Opinion and International Preliminary Report dated Apr. 29, 2008 from International Application No. PCT/EP2007/009879.
PCT International Search Report of PCT/US2012/065712, dated Mar. 29, 2013 (2 pages).
PCT Written Opinion of PCT/US2012/065712, dated Mar. 29, 2013 (5 pages).
PCT International Preliminary Report on Patentability of PCT/EP2007/009879; dated May 19, 2009 (7 pages).
PCT International Search Report of PCT/US2010/027346; dated Oct. 14, 2010 (4 pages).
PCT Written Opinion of the International Searching Authority of PCT/US2010/027346; dated Oct. 14, 2010 (7 pages).
"Changes in the passive electrical properties of human stratum corneum due electroporation" dated Dec. 7, 1994. By U. Pliquett, R. Langer, and J. C. Weaver.
"Electrical properties of the epidermal stratum corneum" dated Aug. 12, 1974. By T. Yamamoto and Y. Yamamoto.
"Non-invasive bioimpedance of intact skin: mathematical modeling and experiments" dated May 2, 2010. By U. Birgersson, E. Birgersson, P. Aberg, I. Nicander, and S. Ollmar.
"Polymer Microneedles for Controlled-Release Drug Delivery" dated Dec. 2, 2005. By J-H. Park, M. G. Allen, and M. R. Prausnitz.
"Utilizing Characteristic Electrical Properties of the Epidermal Skin Layers to Detect Fake Fingers in Biometric Fingerprint Systems—A Pilot Study" dated Dec. 1, 2004. By O. G. Martinsen, S. Clausen, J. B. Nysaether, and S. Grimnes.
"Lack of Pain Associated with Microfabricated Microneedles" dated Oct. 10, 2000. By S. Kaushik, A. H. Hord, D. D. Denson, D. V. McAlliser, S. Smitra, M. G. Allen, and M. R. Prausnitz.
"Insertion of microneedles into skin: measurement and prediction of insertion force and needle facture force" dated Dec. 10, 2003. By S. P. Davis, B. J. Landis, Z. H. Adams, M. G. Allen, and M. R. Prausnitz.
"Microneedle Insertion Force Reduction Using Vibratory Actuation" dated 2004. By M. Yang and J. D. Zahn.
"Two Dimensional Metallic Microelectrode Arrays for Extracellular Stimulation and Recording of Neurons" dated 1993. By A. B. Frazier, D. P. O'Brien, and M. G. Allen.

* cited by examiner

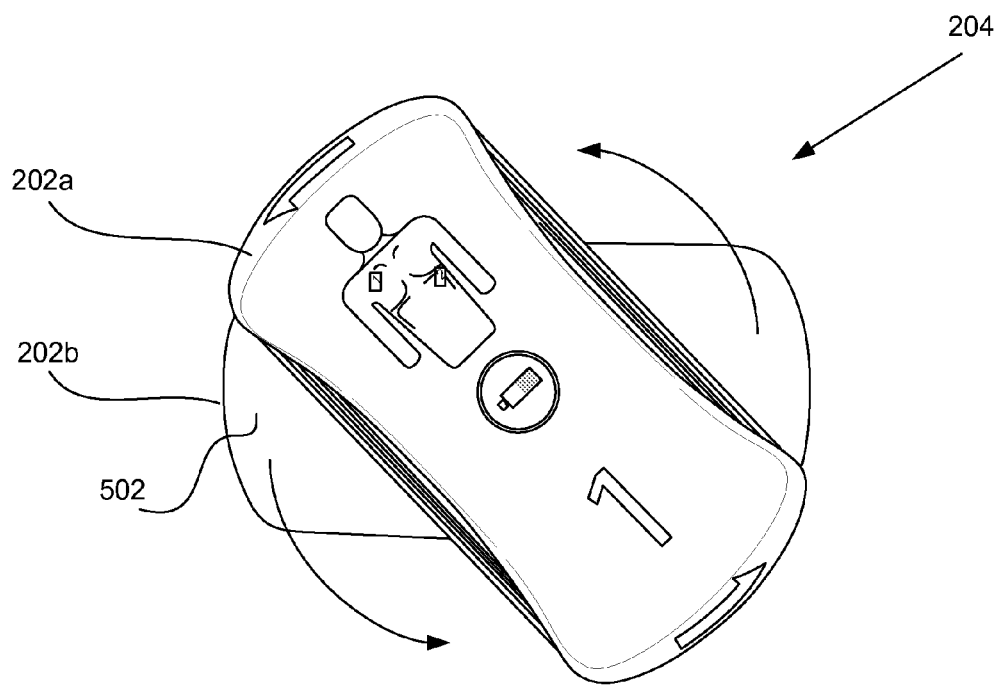
FIG. 5
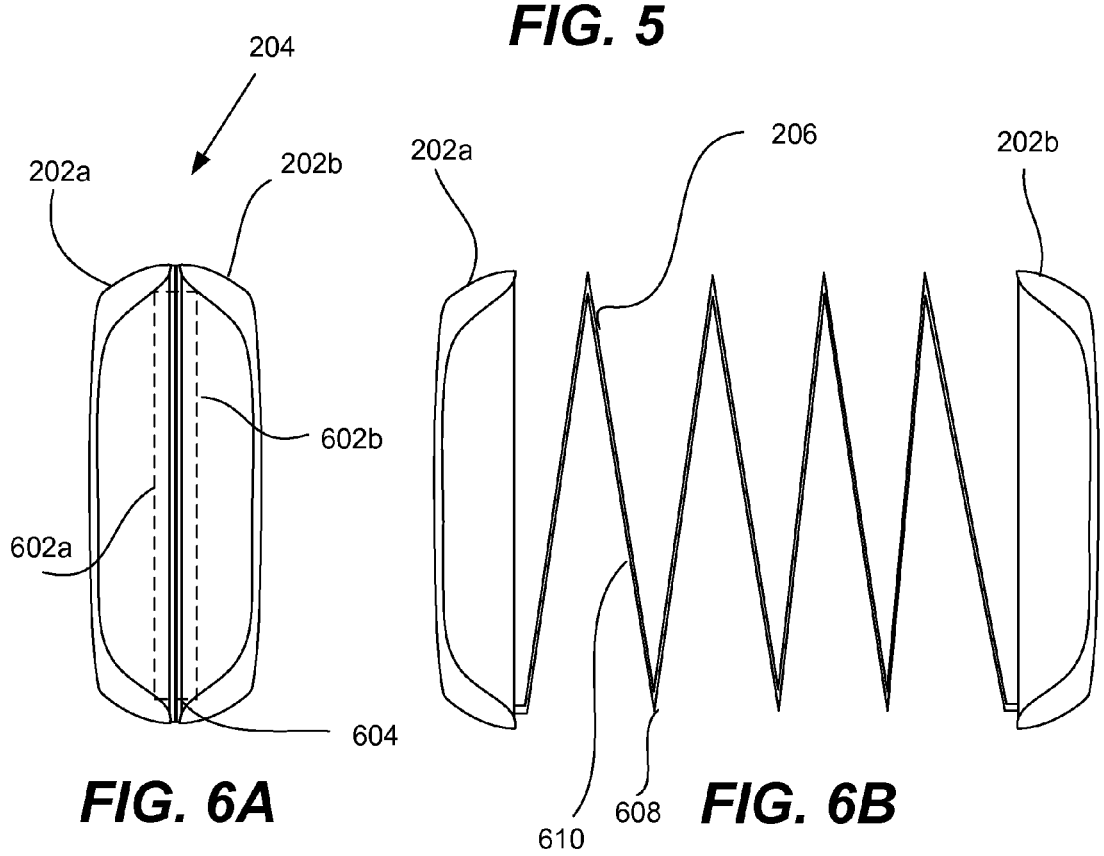
FIG. 6A     FIG. 6B

EXTERNAL DEFIBRILLATOR

CROSS REFERENCE TO RELATED APPLICATIONS

This application claims priority under 35 U.S.C. §119(e) to Provisional Patent Application No. 61/161,014 filed Mar. 17, 2009, entitled "PORTABLE CARDIO DEFIBRILLATOR," which is incorporated herein by reference in its entirety for all purposes.

FIELD OF THE INVENTION

The present invention relates generally to methods and arrangements relating to cardiac medical devices. More specifically, the present invention relates to an external defibrillator.

BACKGROUND OF THE INVENTION

A primary task of the heart is to pump oxygenated, nutrient-rich blood throughout the body. Electrical impulses generated by a portion of the heart regulate the pumping cycle. When the electrical impulses follow a regular and consistent pattern, the heart functions normally and the pumping of blood is optimized. When the electrical impulses of the heart are disrupted (i.e., cardiac arrhythmia), sudden cardiac arrest may result, which inhibits the circulation of blood. As a result, the brain and other critical organs are deprived of nutrients and oxygen. A person experiencing sudden cardiac arrest may suddenly lose consciousness and die shortly thereafter if left untreated.

A well known and effective treatment for sudden cardiac arrest or arrhythmia is defibrillation. Defibrillation involves passing a current through the person to shock the heart back into a normal rhythm. There are a wide variety of defibrillators. For example, implantable cardioverter-defibrillators (ICD) involve surgically implanting wire coils and a generator device within a person. ICDs are typically for people at high risk for a cardiac arrhythmia. When a cardiac arrhythmia is detected, a current is automatically passed through the heart of the user with little or no intervention by a third party.

Another, more common type of defibrillator is the automated external defibrillator (AED). Rather than being implanted, the AED is an external device used by a third party to resuscitate a person who has suffered from sudden cardiac arrest. FIG. 1 illustrates a conventional AED 100, which includes a base unit 102 and two pads 104. Sometimes paddles with handles are used instead of the pads 104. The pads 104 are connected to the base unit 102 using electrical cables 106.

A typical protocol for using the AED 100 is as follows. Initially, the person who has suffered from sudden cardiac arrest is placed on the floor. Clothing is removed to reveal the person's chest 108. The pads 104 are applied to appropriate locations on the chest 108, as illustrated in FIG. 1. The electrical system within the base unit 100 generates a high voltage between the two pads 104, which delivers an electrical shock to the person. Ideally, the shock restores a normal cardiac rhythm. In some cases, multiple shocks are required.

Although existing technologies work well, there are continuing efforts to improve the effectiveness, safety and usability of automatic external defibrillators.

SUMMARY OF THE INVENTION

The present invention relates to a variety of methods and arrangements for improving the portability, accessibility and performance of a defibrillator. In one aspect of the present invention, a defibrillator including two sealed paddles is described. Each paddle includes a defibrillator electrode covered in a protective housing. The two paddles are sealed together using a releasable seal to form a paddle module such that the housings of the paddles form the exterior of the paddle module. An electrical system including at least a battery and a capacitor is electrically coupled with the paddles. The capacitor is arranged to apply a voltage at the defibrillator electrodes, which helps generate an electrical shock suitable for arresting a cardiac arrhythmia.

Various actions may be triggered by the opening of the seal. For example, in some embodiments the opening of the seal automatically causes the capacitor to be charged by the battery. After the seal has been opened, a wireless message may be sent to a suitable device (e.g., a telephone, a cell phone, a remote server, etc.) at an emergency care facility. The message may contain important information relating to the identity of the user, the location of the defibrillator and the condition of the person who is being defibrillated.

Any capacitors and batteries in the electrical system of the defibrillator may be stored in a single paddle, both paddles or distributed across various discrete devices. In some designs, all capacitors and batteries are stored only in one or both of the paddles. Other designs involve placing at least a portion of the electrical system in a separate power module. The power module may be linked to one or more of the paddles with a cable. In some implementations, the power module and paddle module may be attached to a belt.

One aspect of the invention involves a connecting structure that physically and electrically connects two defibrillator paddles and also plays an instructional role. The flexible connecting structure includes one or more sheet-like sections. There are instructions for properly using the defibrillator on a surface of the connecting structure. The instructions may be conveyed in a wide variety of ways, including audio prompts, electronic text, lighting patterns, etc. Generally, the flexible connecting structure is arranged to be easy for a user to reference while the user is simultaneously operating the defibrillator.

In another aspect of the invention, a defibrillator with pads that each have electrically conductive protrusions will be described. Each pad has a defibrillator electrode that includes the electrically conductive protrusions. An electrical system including at least a battery and a capacitor is coupled with the two pads. Generally, the electrical system also may include an electrical control system that helps convert the energy from the battery to a voltage that charges that capacitor. The control system may also help regulate the flow of current from the capacitor to the load and/or help perform cardiac rhythm detection by analyzing signals received through the pads. In some embodiments, the electrically conductive protrusions on each pad are sharp, densely arranged, bristle-like and/or suitable for penetrating into the skin of a cardiac arrest victim. By pressing into the skin of the person, the protrusions may help reduce the electrical resistance of the skin. Therefore, defibrillation may be possible at lower voltage levels. This design may be combined with other aforementioned embodiments. For example, the electrically conductive protrusions may be sealed within a paddle module that is formed by sealing together the two paddles. An added advantage of such an approach is that it helps to ensure the sterility and safety of the protrusions.

Additional embodiments relate to methods for using the above defibrillator designs.

BRIEF DESCRIPTION OF THE DRAWINGS

The invention and the advantages thereof, may best be understood by reference to the following description taken in conjunction with the accompanying drawings in which:

FIG. 5 illustrates a diagrammatic top view of a paddle module while the paddle module is being unsealed in accordance with a particular embodiment of the present invention.

FIGS. 6A and 6B illustrate diagrammatic side views of a sealed and unsealed paddle module in accordance with a particular embodiment of the present invention.

In the drawings, like reference numerals are sometimes used to designate like structural elements. It should also be appreciated that the depictions in the figures are diagrammatic and not to scale.

DETAILED DESCRIPTION OF THE PREFERRED EMBODIMENTS

The present invention relates generally to methods and arrangement for arresting a cardiac arrhythmia using an external defibrillator. Some aspects of the invention relate to defibrillators with various types of arrangements, connecting structures, and electrodes.

The steady circulation of blood is crucial to the proper functioning of the human body. The circulation of blood is governed by the heart, whose expansion and contraction is in turn controlled by a regular pattern of electrical impulses. When this pattern of electrical impulses becomes chaotic or overly rapid, a sudden cardiac arrest may take place. Tragically, the victim typically collapses and dies unless he or she receives proper medical attention.

The most successful therapy for sudden cardiac arrest is prompt and appropriate defibrillation. A defibrillator uses electrical shocks to restore the proper functioning of the heart. A crucial component of the success or failure of defibrillation, however, is time. Ideally, a victim should be defibrillated immediately upon suffering a sudden cardiac arrest, as the victim's chances of survival dwindle rapidly for every minute without treatment.

Accordingly, efforts have been made to improve the availability of automated external defibrillators (AED), so that they are more likely to be in the vicinity of sudden cardiac arrest victims. Advances in medical technology have reduced the cost and size of automated external defibrillators (AED). Some modern AEDs approximate the size of a laptop computer or backpack. Even small devices may typically weigh 10 pounds or more. Accordingly, they are increasingly found mounted in public facilities (e.g., airports, schools, gyms, etc.) and, more rarely, residences. Unfortunately, success rates for cardiac resuscitation remain abysmally low (less than 1%.)

Such solutions, while effective, are still less than ideal for most situations. Assume, for example, that a person suffers from a cardiac arrest in an airport in which multiple AEDs have been distributed. The victim's companion would nevertheless have to locate and run towards the nearest AED, pull the device off the wall, and return to the collapsed victim to render assistance. During that time, precious minutes may have passed. According to some estimates, the chance of surviving a sudden cardiac arrest is 90% if the victim is defibrillated within one minute, but declines by 10% for every minute thereafter. A defibrillator design that reduces the time to defibrillation by even two to three minutes will save more lives.

Figure 1:
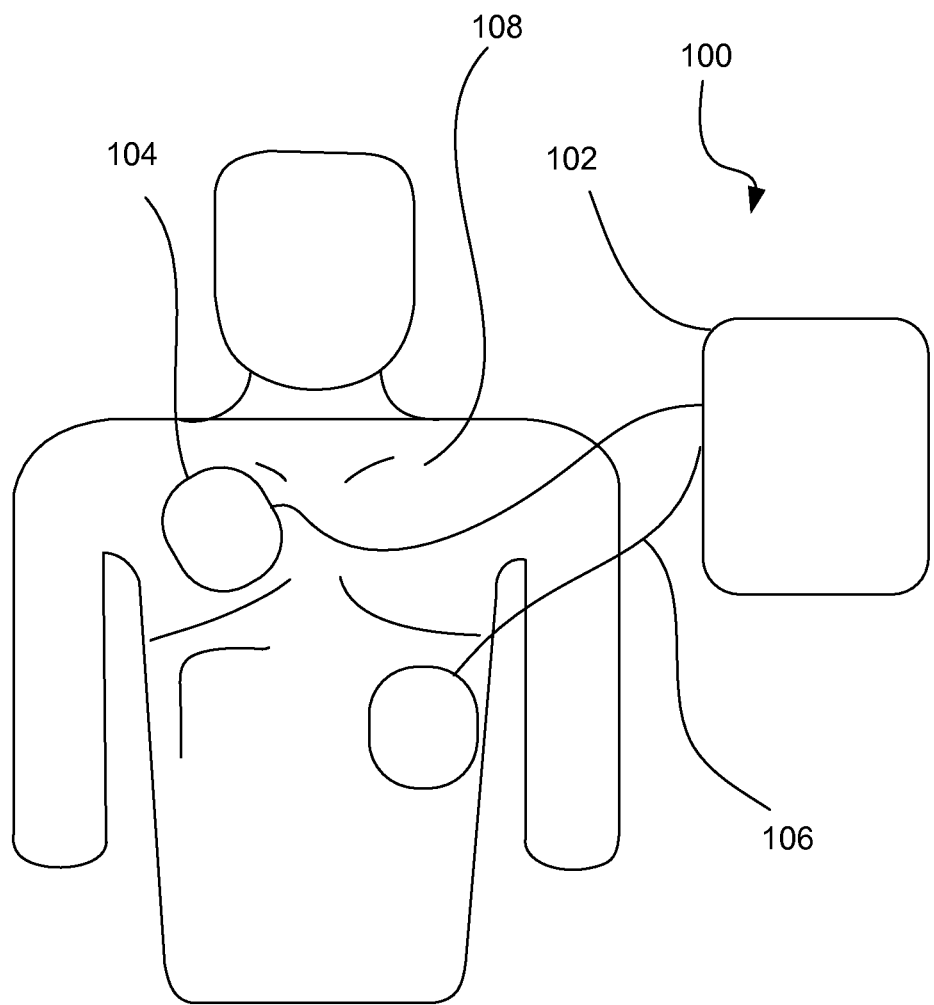
FIG. 1 diagrammatically illustrates an example of a conventional defibrillator.

An additional challenge is that a sudden cardiac arrest may take place anywhere. People often spend time away from public facilities and their homes. For example, a sudden cardiac arrest could strike someone while biking in the hills, skiing on the mountains, strolling along the beach, or jogging on a dirt trail. Ideally, an improved AED design would be compact, light, and resistant to the elements and easily attached or detached from one's body. The typical AED design illustrated in FIG. 1, which includes a sizable console or power unit whose form factor is similar to that of a laptop or backpack, seems less than ideal for the outdoors and other rigorous environments.

There are also improvements to be made in the area of usability. As noted above, every minute of delay or distraction can substantially decrease the victim's probability of survival. As a result, it is generally beneficial to streamline the operation of the defibrillator so that a user of the defibrillator, who is presumably under substantial mental duress, can focus his or her attention on a few, key variables. That is, aside from delivering a proper shock and monitoring the victim, a user of the defibrillator would ideally not have to worry whether the defibrillator is sterile, has been tampered with or is charged and ready to use. Additionally, during a time of crisis, the user ideally would not have to be concerned about contacting medical personnel, transmitting important information relating to location, the condition of the victim, etc.

Accordingly, the present invention relates to various defibrillators with features to deal with one or more of the above concerns. Various implementations involve a sealed paddle module that is split apart to form defibrillator paddles that can be placed on the chest of a victim to arrest a cardiac arrhythmia. A frangible seal may be permanently deformed by the opening of the paddle, which helps indicate whether the paddle module is has already been used. One or more critical functions e.g., the charging of the defibrillator capacitors, the sending of GPS/health information, etc., may be triggered by the opening of the seal. Various embodiments are one-use (i.e., suitable for arresting a cardiac arrhythmia in one rather than many people), which allows the defibrillator to have a smaller power system and therefore be more compact. Some approaches involve conductive protrusions on the defibrillator electrodes, which facilitates the flow of current through the chest of the victim, thereby helping to reduce the power requirements of the defibrillator and further decrease its size. In some implementations, the defibrillator includes a connecting structure that extends between the paddles and helps instruct the user in the proper operation of the defibrillator. These and other embodiments will be discussed in more detail in the specification below.

Figure 2A:
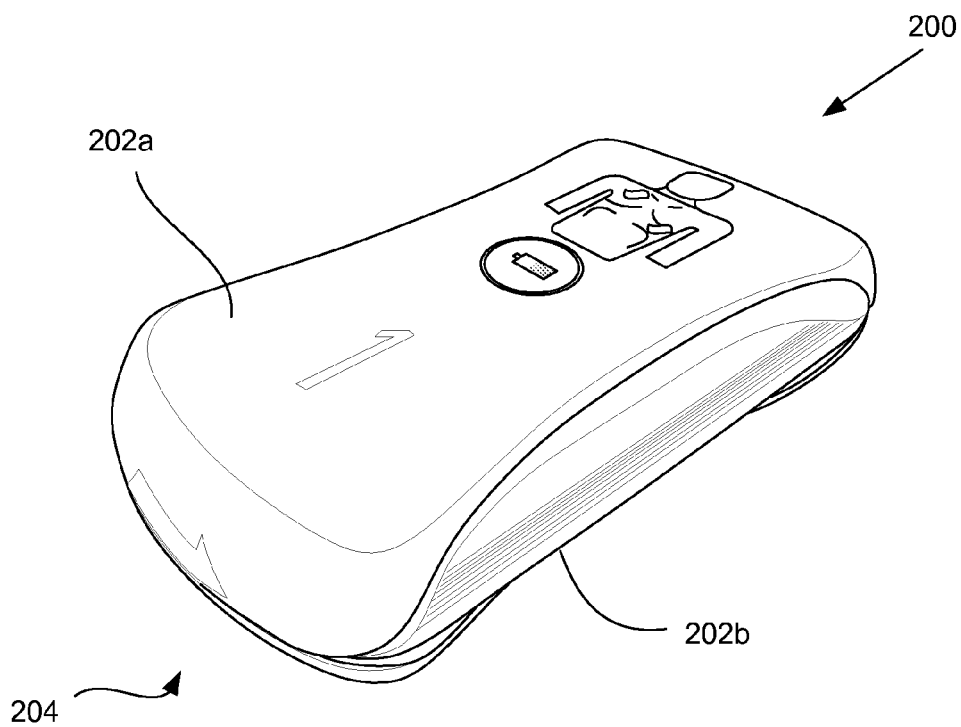
FIG. 2A illustrates a diagrammatic perspective view of a paddle module in accordance with a particular embodiment of the present invention.
Figure 2B:
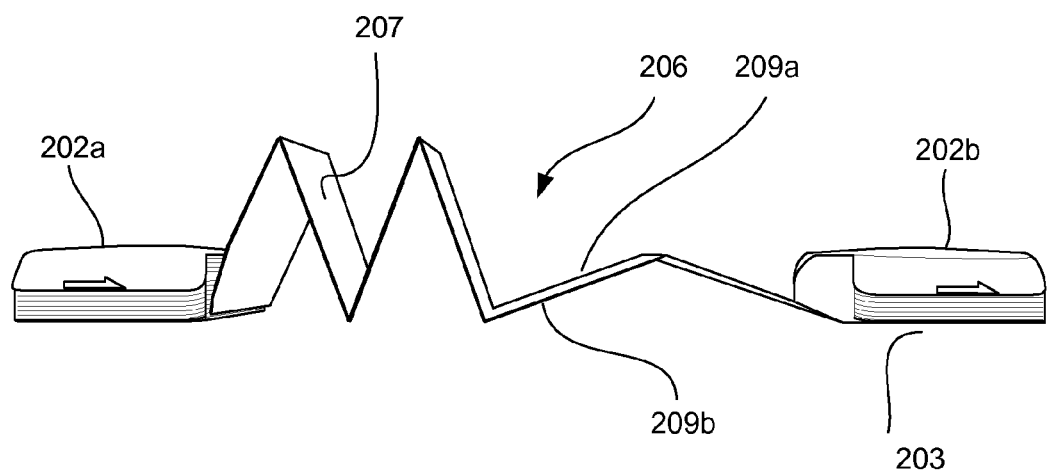
FIG. 2B illustrates a diagrammatic side view of defibrillator paddles and a connecting structure in accordance with a particular embodiment of the present invention.

Initially, with reference to FIGS. 2A and 2B, an exemplary defibrillator 200 according to one embodiment of the invention will be described. The defibrillator 200 includes two defibrillator paddles 202a and 202b that are mounted over one another and directly sealed together to form a paddle module 204. When a need arises to defibrillate a victim of sudden cardiac arrest, the paddles 202a and 202b may be pulled apart, which reveals a connecting structure 206, as seen as FIG. 2B, which physically and electrically connects the paddles. The connecting structure 206 may include a sheet-like portion 207 with instructions that help a user operate the defibrillator 200.

Preferably, the paddles 202a and 202b are directly sealed together with a frangible seal. That is, when the paddles 202a and 202b are first pulled apart from one another, the seal is irreversibly and permanently deformed. This feature can have several useful applications. A deformed seal helps indicate whether the paddles 202a and 202b have been used before, which in turn helps indicate whether they are sterile or have sufficient power. Additionally, various events may be triggered by the breaking of the seal. For example, when the seal is broken, one or more capacitors in the defibrillator 200 may start charging without requiring additional input from the user (i.e., a button or other mechanical switch need not be separately triggered to power up the defibrillator.) Upon the opening of the paddle module 204, personal data of the owner of the defibrillator 200 and/or GPS data indicating the location of the defibrillator 200 may be automatically and wirelessly sent to a remote device or server. As a result, medical personnel, family members or other important individuals can be informed automatically and immediately about the use of the defibrillator.

The connecting structure 206 may serve the dual purpose of displaying useful information as well as electrically connecting the paddles 202a and 202b. In some existing AEDs, paddles or patches are individually connected to a base unit with cables. Instructions are typically displayed on the base unit. The base unit and its display, however, take up considerable space in such systems. In the illustrated embodiment, at least some of the instructions are provided on a flexible connecting structure 206 that is compressed between the paddles 202a and 202b when the paddle module 204 is sealed. When the paddle module 204 and the paddles 202 and 202b are pulled apart, the connecting structure 206 unfolds or otherwise decompresses and extends between the paddles 202a and 202b.

The connecting structure 206 is attached to the defibrillator paddles 202a and 202b such that it is easily viewable and can be used as an instructional tool while the user is operating the defibrillator. In the illustrated embodiment, for example, each defibrillator paddle 202a has a defibrillator electrode with an electrically conductive contact surface 203. At the appropriate time, high voltage may be applied at the contact surfaces 203 to deliver an electrical shock. Each sheet-like section 207 of the connecting structure 206 includes a top surface 209a and an opposing bottom surface 209b. The top surface 209a may include images, light emitting devices, light reflecting devices, display screens, electronic display devices, etc. that help instruct the user in the proper operation of the defibrillator. As seen in FIG. 2B, when the defibrillator paddles 202a and 202b are spread out and the conductive contact surfaces 203 of the paddles face downward, instructions on the top surface 209a of the connecting structure 206 tend to face upward. Thus, a user of the defibrillator may easily reference the connecting structure 206 for further instructions and step-by-step guidance while holding the defibrillators over the chest of the victim.

In some embodiments, the portability of the defibrillator 200 may be enhanced by incorporating some or all of the electrical system of the defibrillator into the paddle module 204. While some implementations involve connecting the paddle module 204 via a cable to an external power module, various other approaches involve placing all of the capacitors and batteries of the defibrillator 200 within the housings of the paddles 202a and 202b. Such designs may free the two paddles 202a and 202b from having to connect with a separate third device, which may help make the defibrillator 200 more convenient to carry, access and operate.

Generally, the overall volume of the defibrillator 200 is influenced by the capacity of its electrical system. A defibrillator that is capable of delivering more shocks and charging the capacitors more times generally has more and/or larger batteries. More specifically, a larger battery can typically support a greater number of electrical shocks than a smaller one before requiring replacement or recharging. As far as the inventors are aware, existing AEDs have the capacity to deliver many shocks e.g., at least 50 shocks or many more than are typically needed to treat a single cardiac arrest victim.

While having such a high capacity electrical system is generally perceived as beneficial, this conventional approach may also contribute to a larger and less portable defibrillator. Accordingly, some conventional AEDs have the bulk weight and form factor of a small briefcase, backpack or laptop. Such designs, however, while easily mountable on a wall or carried in a large backpack, are not as easily hung on a belt or carried in a pocket or purse. A higher degree of portability may allow people to comfortably carry the defibrillator while jogging, hiking or biking in remote areas. A defibrillator that is conveniently carried in a pocket, purse or belt is more likely to be carried on one's person and thus be immediately accessible in the event that the carrier is a first responder, such as a paramedic, police officer, medic or even a nurse in a hospital, emphasizing that the first few minutes are critical should a nearby person experience a sudden cardiac arrest.

To reduce the size of the associated electrical system and improve portability, the present invention contemplates a defibrillator that is arranged to treat a single cardiac arrest victim. Accordingly, some embodiments involve a defibrillator 200 that is arranged to deliver no more than five (5) electrical shocks to arrest a cardiac arrhythmia. Five (5) shocks are believed to be generally sufficient to address cardiac arrhythmia in a single individual, although the exact limitation may vary (e.g., no more than 4 to 10 shocks.) In some implementations, the limitation is enforced by software (e.g., computer code that counts the number of delivered shocks and prevents any additional charging of a capacitor, the delivery of more shocks to the defibrillator electrodes, etc.), hardware (e.g., limitations based on the physical size or specifications of a capacitor or battery, etc.) or both. Some designs involve a defibrillator in which the volume of the entire defibrillator is less than approximately 550 cubic centimeters and/or the volume of all the capacitors in the defibrillator is less than approximately 450 cubic centimeters. By way of comparison, some conventional, portable AEDs have a volume in excess of 9000 cubic centimeters. It should be appreciated that the defibrillator, even if only initially partially successful (i.e., the patient relapses into an unstable rhythm) may provide a critical "bridge" of therapy until the arrival of paramedics or professionally trained personnel. Some designs require that any defibrillator used to defibrillate a single individual be submitted to a technician to be refurbished (e.g., to replace a capacitor in the defibrillator) or reprogrammed before it can be used again to defibrillate someone else. This helps ensure the regular maintenance, charging and/or sterilization of the defibrillator.

Figure 3A:
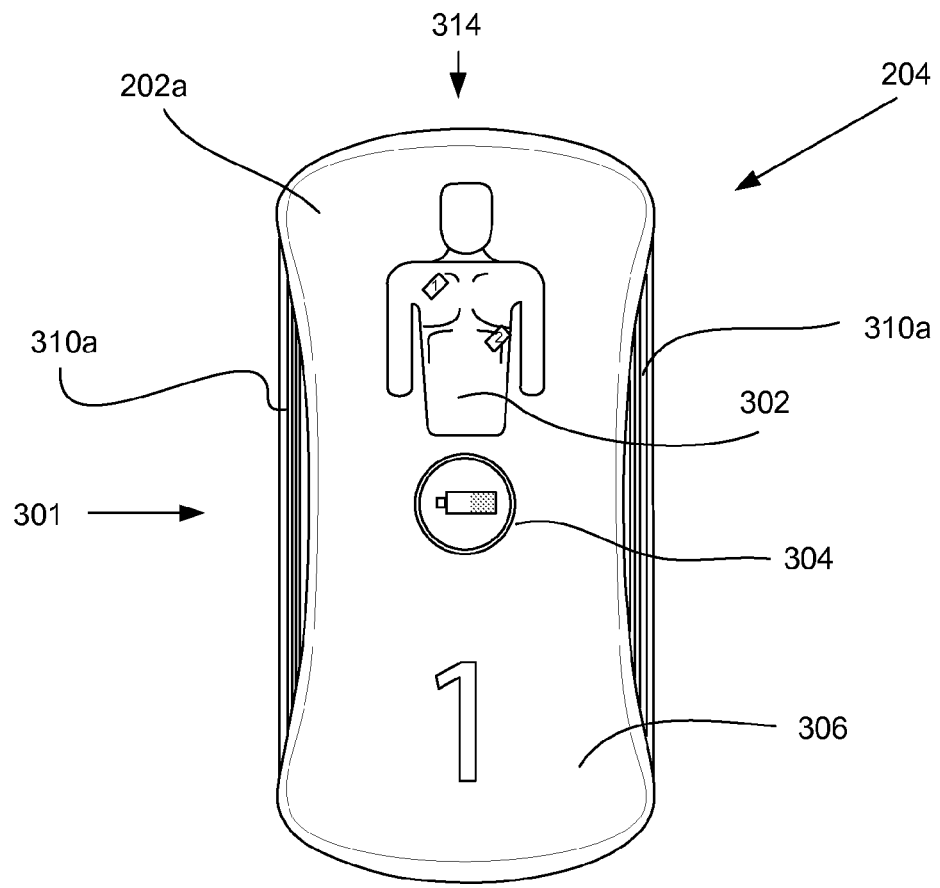
FIGS. 3A and 3B illustrates diagrammatic top and side views of a paddle module in accordance with a particular embodiment of the present invention.

Referring now to FIG. 3A, a top view of an exemplary paddle module 204 will be described. More specifically, FIG. 3A illustrates the outer housing 306 of one of the defibrillator paddles 202a, which together with the second defibrillator paddle 202b helps form the outer housing of the paddle module 204. The exterior housing 306 of the paddle 202a may be used to convey a wide variety of useful information to a user using any suitable medium or technology. By way of example, as shown in FIG. 3A, the housing 306 may include a first instructive image 302 that helps a user properly position the defibrillator paddle 202a on the chest of a sudden cardiac arrest victim. A second instructive image 304 may help indicate whether the battery of the defibrillator is fully charged. The housing of the defibrillator paddle 202a may incorporate a wide variety of technologies to convey messages to the user, including buttons, switches, LEDs, display screens, speakers, etc. To use a simple example, the second instructive image 304, which depicts a battery symbol, may be superimposed over an LED and a mechanical lever. Accordingly, the second instructive image 304 may emit light and flash when pushed to indicate whether the battery of the defibrillator is sufficiently charged. Different colored lights, flashing frequencies and/or speeds may help convey additional details e.g., whether the battery power is low, requires maintenance, is fully charged, etc. In another example, a display screen and/or speaker (not shown) may be exposed and mounted on the housing 306 to help communicate with the user of the defibrillator using electronic images and audio cues, respectively.

The outer housing 306 may be designed in a wide variety of ways, depending on the needs of a particular application. The housing 306 may be formed from any resilient material, such as a hard plastic, composite, etc. Some housing designs enhance the comfort and convenience in carrying the paddle module 204. When a person is engaged in a vigorous activity such as jogging and is carrying a sharp-edged object in his or her pocket, the sharp edges of the object can uncomfortably dig into the sides of the person. Additionally, a person may store the paddle module 204 amidst many other objects in a larger container, such as a purse. Under such circumstances, protrusions and recesses on the housing can trap particles and catch on other items. Thus, some designs for the paddle module 204 involve a generally smooth, rounded exterior without any deep recesses (e.g., a recess whose depth is greater than 4 mm) or sharp edges. Accordingly, the present invention contemplates a great many other configurations and is not limited to the above examples.

Figure 3B:
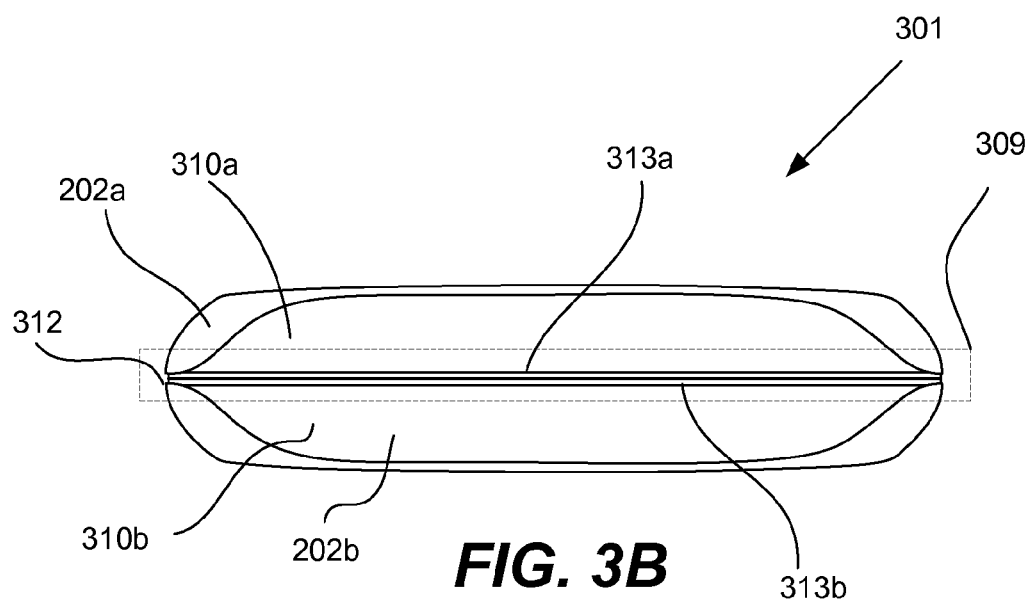

Referring now to FIG. 3B, a side view 301 of the paddle module 204 will be described. In the illustrated embodiment, the first defibrillator paddle 202a is positioned over the second defibrillator paddle 202b. The defibrillator paddles 202a and 202b are sealed together using a frangible seal 312. The side of each defibrillator paddle 202a and 202b includes a gripping region 310a and 310b, respectively, which is arranged to help a user firmly hold the defibrillator paddle.

Generally, the paddle module 204 is sealed in a manner that protects electrically conductive elements in the defibrillator while reducing the number of components that must be handled to operate the defibrillator. In the illustrated embodiment, for example, the seal 312 is arranged such that the electrically conductive contact surfaces 313a and 313b of the defibrillator paddles 202a and 202b are facing one another, attached with one another and are hidden within the sealed paddle module 204. Various designs involve a seal that is entirely hidden within the housing of the paddle module 204. In some embodiments, the seal 312 extends along a strip 309 around the perimeter of the paddle module 204. In still other embodiments, the outer housing of the individual paddles 202a and 202b may form the majority, if not substantially all, of the exposed surface area of the paddle module 204.

The frangible seal 312 helps indicate whether the paddle module 204 has ever been opened or tampered with. Preferably, breaking or opening the seal requires permanently and irreversibly deforming the seal 312 e.g., physical tearing of an adhesive, tape or other bonding material. Any suitable material or mechanism may used to form or support the seal 312, including a magnetic lock, a tape, an adhesive, a latch, a pin, etc. It is also preferable that the seal 312 is water resistant and helps prevent undesirable liquids and/or dust from penetrating into the interior of the paddle module 204 at the region where the defibrillator paddles 202a and 202b interface with one another.

Figure 3C:
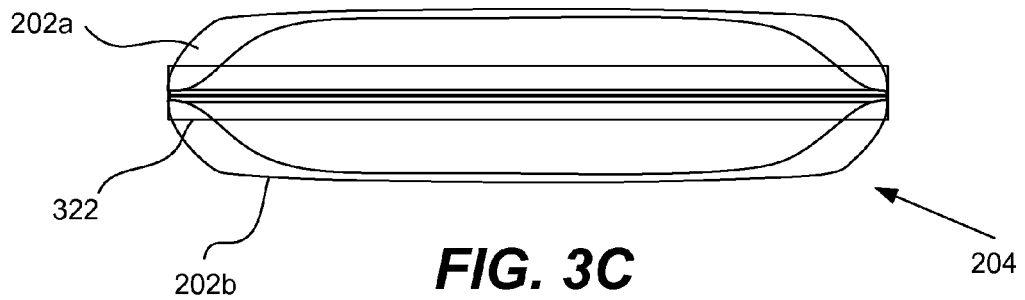
FIG. 3C-3F illustrates different approaches to sealing the paddle module in accordance with various embodiments of the present invention.
Figure 3D:
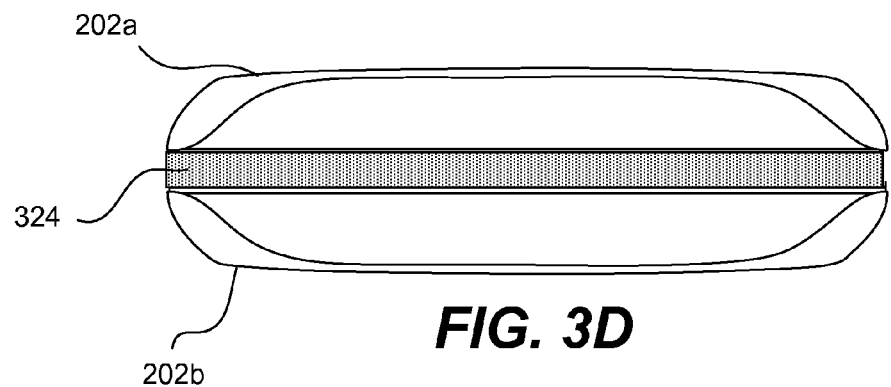
Figure 3E:
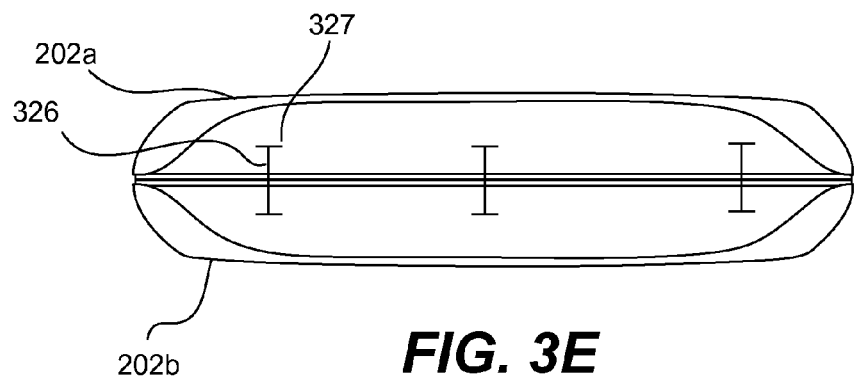
Figure 3F:
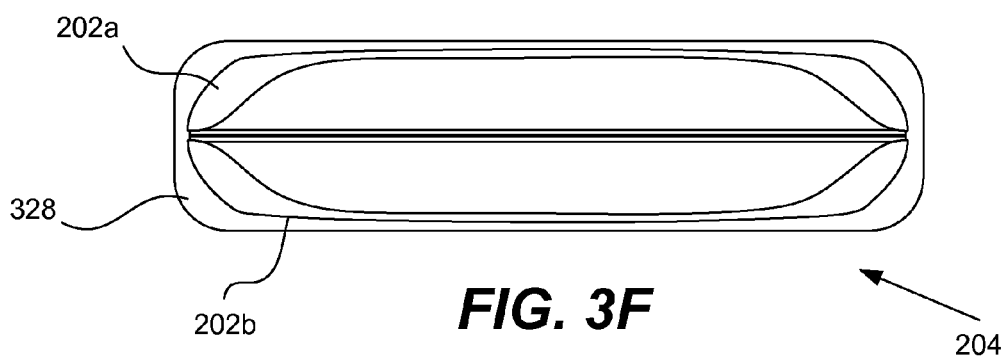

The defibrillator paddles 202a and 202b may be sealed together using any suitable means or structure. FIGS. 3C-3F illustrates several exemplary approaches, although many more are possible. FIG. 3C illustrates an adhesive tape 322 that is wrapped around the perimeter of the paddle module 204. The tape 322 is positioned along the interface between the defibrillator paddles 202a and 202b and helps secure the paddles to one another. Preferably, the opening of the paddle module 204 requires a physical tearing of the tape 322. In FIG. 3D, a paddle interface 324 is inserted directly between the paddles 202a and 202b. Rather than being directly secured to one another, the defibrillator paddles 202a and 202b are each positioned on opposite sides of the paddle interface 324 and are secured thereto. The paddle interface 324 may include a slot, recess and/or opening that allows a connecting structure (not shown) to extend between the paddles. In some implementations, the paddle interface 324 contains no internal electrical circuitry and/or is meant to be discarded once the paddles are released from the paddle interface 324. In the illustrated embodiment, the paddle interface 324 is small relative to either paddle (e.g., has smaller dimensions and/or volume) and forms a continuous outer surface with the housings of the attached paddles. FIG. 3E illustrates an embodiment in which the seal between the defibrillator paddles 202a and 202b is supported at least in part by pins 326. The pins 326 extend through bottom surfaces of the defibrillator paddles 202a and 202b and are firmly secured to each of the paddles using corresponding anchors 327. When the paddle module 204 is opened, the pins 326 may be broken or severed. In some embodiments, sensors are coupled with the pins 326 and arranged to detect the breaking of the pins 326. This information is then passed on to a processor in the defibrillator and used to initiate follow-on actions, as described later in the present application. In FIG. 3F, the defibrillator paddles 202a and 202b are sealed together using an external housing 328. Although the external housing 328 of FIG. 3F is depicted as entirely encapsulating the defibrillator paddles 202a and 202b, in other embodiments the external housing 328 only covers portions of the sealed paddles. Generally, separating the defibrillator paddles 202a and 202b requires first opening or releasing the external housing 328. The external housing 328 may be made of any suitably lightweight, resilient material, such as plastic, ceramic, etc. and may be watertight. To minimize the weight and size of the external housing 328, it may be arranged to form-fit the defibrillator paddles 202a and 202b. Accordingly, when the paddles are sealed within the external housing 328, the distance between an exterior surface of one of the paddles and an exterior surface of the external housing may be quite small (e.g., less than 2 cm.) Generally, electrical components of the defibrillator that are necessary for defibrillation are not situated within the external housing 328, which in some implementations is meant to be discarded after it has been opened.

In some implementations, any opening of the seal that secures the defibrillator paddles to one another (e.g., the opening of the frangible seal 312 of FIG. 3B, the tearing of the tape 322 in FIG. 3C, the breaking away of the paddles from the paddle interface 324 of FIG. 3D, the breaking of a pin 326 of FIG. 3E and the opening of the external housing 328 of FIG. 3F, etc.) is detected and communicated by one or more sensors in the defibrillator. A wide variety of sensors may be used to detect the opening of the seal 312, including pressure sensors, electrical sensors, etc. In a preferred embodiment, a sensor generates signals to inform a processor in the defibrillator of the opening of the seal. Based on the sensor output, a variety of additional operations may be triggered within the defibrillator. For example, once the seal has been broken, one or more capacitors of the defibrillator may be automatically charged. In another embodiment, the opening of the seal triggers the sending of a wireless message to a remote server. The wireless message can include any appropriate information e.g., the GPS-determined location of the defibrillator approximately at the time of the breaking of the seal, contact information (e.g., name and cell phone number), etc. Thus, the user, who is preoccupied with caring for the victim of a sudden cardiac arrest, does not have spend time and energy notifying suitable personnel of the emergency.

Returning to FIGS. 3A and 3B, optional features for improving the grip of a person on the defibrillator paddles 202a and 202b will be described. In the illustrated embodiment, the gripping regions 310a and 310b are arranged in a manner that helps the user firmly hold the defibrillator paddles 202a and 202b. Each gripping region 310a and 310b may include one or more grooves for receiving a thumb or fingers. Preferably, the gripping region 310a is situated on either side of each defibrillator paddle, as illustrated in FIG. 3A, so that the gripping regions can comfortably receive a hand that is curled around the paddle. To help reduce the chance of slippage, each gripping region may include ribbing, recesses, a flexible material (e.g., a flexible plastic, rubber, etc.) and/or any other suitably textured surface. Still other embodiments involve handles that extend out of each defibrillator paddle 202a and 202b. When the defibrillator paddles 202a and 202b are sealed together as a paddle module 204, the handles, which may form various shapes (e.g., a full loop, partial loop, a wedge, etc.), may extend out of the paddle module 204 in opposite directions and/or be symmetrically arranged relative to one another.

Figure 4A:
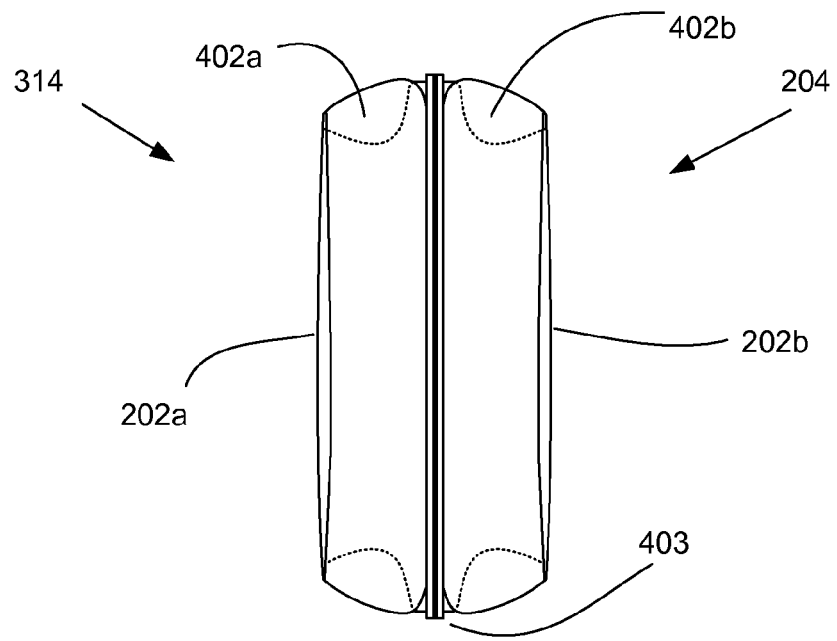
FIG. 4A illustrates a diagrammatic end view of a paddle module in accordance with a particular embodiment of the present invention.

Referring now to FIG. 4A, another cross-sectional view of the paddle module 204 is illustrated. Rather than a lengthwise view, FIG. 4A illustrates a cross-sectional view from one end 314 of the paddle module 204, as indicated in FIG. 3A. This view better illustrates the contour of the grooved gripping region 310a and 310b. In the illustrated embodiment, the grooves 402a and 402b of defibrillator paddles 202a and 202b are arranged symmetrically to receive thumbs of a user and facilitate the holding and breaking apart of the paddles. A raised edge of each groove 402a and 402b may cooperate to form a central ridge 403 that extends along a central axis of the paddle module 204.

Figure 4B:
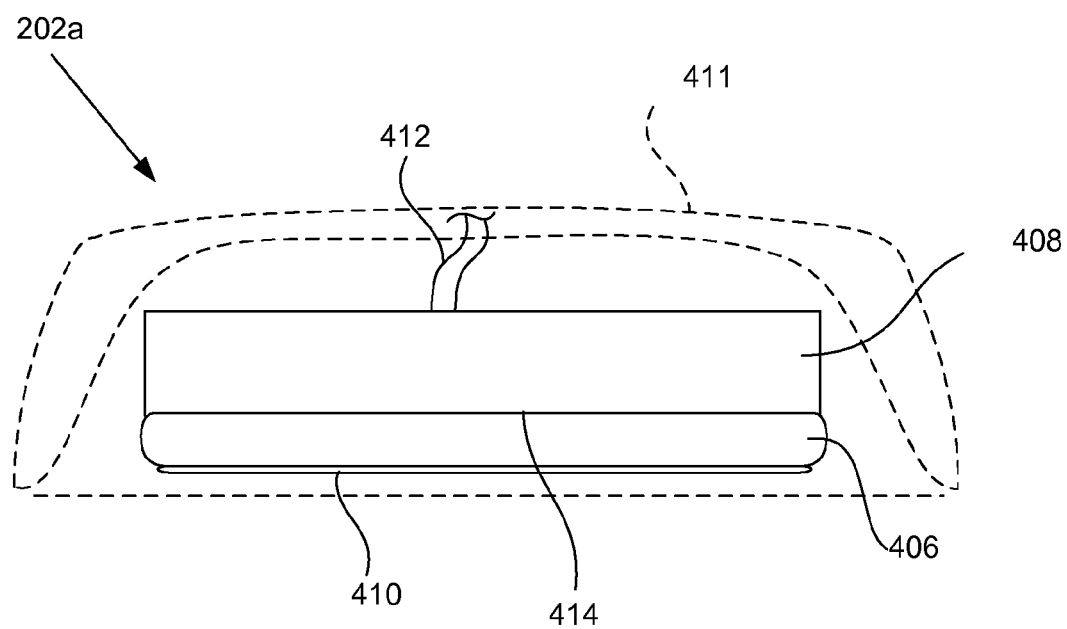
FIG. 4B illustrates a diagrammatic side view of components of a defibrillator paddle in accordance with a particular embodiment of the present invention.

Referring next to FIG. 4B, various internal components of one of the defibrillator paddles 202a will be described. In the illustrated embodiment, defibrillator paddle 202a includes an outer housing 411, a defibrillator electrode 408, a conductive gel 406 and an adhesive 410. If the defibrillator includes an external power module, an external power cable 412 may couple the defibrillator electrode 408 with the external power module. In another embodiment, there is no external power cable 412 and no external power module to connect to. In that case, the defibrillator paddle 202a may incorporate some or all of the functionality of the power module into itself, and thus may include additional electrical components (e.g., one or more capacitors, batteries, etc.)

The defibrillator electrode 408 is used to generate a high voltage suitable for helping to arrest a cardiac arrhythmia in a person. To generate the high voltage, the defibrillator electrode 408 is coupled with one or more capacitors, which release their charge to deliver an electrical shock through the defibrillator electrode 408. The duration, voltage and waveform characteristics of the electrical shock may vary widely. By way of example, the electrical shock may involve a biphasic discharge between approximately 150 and 250 joules. During the electrical shock, a voltage differential of approximately 1400 to 2000 volts may be generated between the two defibrillator electrodes 408 of the two defibrillator paddles.

Although the above voltage differentials work well, various implementations contemplate a voltage differential as high as 5000 volts.

An electrically conductive gel 406 may be positioned on a contact surface 414 of the defibrillator electrode 408. The conductive gel 406 is flexible and better conforms to the contours of the human body. By increasing the contact surface area, the conductive gel 406 facilitates the flow of current from the defibrillator electrode 408 through the chest of a victim of sudden cardiac arrest. An electrically conductive adhesive 410 may be positioned on the conductive gel 406, which helps further strengthen the conductive connection between the chest of the victim and the defibrillator paddle 202*a*.

Referring now to FIG. 5, various embodiments relating to the opening of the paddle module 204 will be described. Partially opened paddle module 204 includes defibrillator paddles 202*a* and 202*b*. In the illustrated embodiment, the seal (not shown) that previously bonded the defibrillator paddles 202*a* and 202*b* together is being broken using a twisting motion. That is, the seal is arranged to be released by rotating the defibrillator paddle 202*a* in a direction that is substantially parallel to a contact surface 502 on the defibrillator paddle 202*b*. Preferably, the seal is arranged to not open under the stresses of everyday carrying, but opens relatively easily when force is applied in a deliberate manner. By way of example, some embodiments feature a seal that does not break when force external to the paddle module 204 is applied to pull the sealed defibrillator paddles 202*a* and 202*b* directly apart (e.g., in a direction perpendicular to the contact surface 502 of the defibrillator paddle 102*b*), but that does break when the same amount of external force is applied in a twisting or rotating motion (e.g., in a direction that is parallel to the contact surface 502.)

Although FIG. 5 illustrates the use of a twisting motion to break the seal of the paddle module 204, some designs contemplate different opening motions. For example, the opening of the seal may be triggered by the pressing of a mechanical lever or switch on an exterior surface of one or both of the defibrillator paddles 202*a* and 202*b*. Some implementations require that such pressing is combined with a force that pulls apart the paddles and/or twists the paddles. In other embodiments, the seal is broken by pulling a tab or pulling a strip around the sides and/or periphery of the paddle module 204. In still another implementation, the seal is broken by squeezing seal release levers on one or more sides of the paddle module 204.

Referring next to FIG. 6A, an embodiment of a paddle module 204 with an embedded connecting structure 206 will be described. FIG. 6A illustrates a sealed paddle module 204, which includes defibrillator paddles 202*a* and 202*b*. Each defibrillator paddle 202*a* and 202*b* may include an optional recess 602*a* and 602*b*. The defibrillator paddles 202*a* and 202*b* are mounted over one another such that their respective recesses 602*a* and 602*b* cooperate to form a cavity 604, which may be entirely hidden within and sealed inside the paddle module 204. The cavity 604 contains the connecting structure 206, which physically and electrically connects the two defibrillator paddles 202*a* and 202*b*. Therefore, while the paddle module 204 remains sealed, the connecting structure 206 is unexposed and disposed directly between the two defibrillator paddles 202*a* and 202*b*.

Within the cavity 604, the connecting structure 206 is in a compressed form. This compressed form may involve folding, coiling and any other suitable form of compression, depending on the physical characteristics of the connecting structure 206. By way of example, in the illustrated embodiment, the connecting structure 206 is compressed between the sealed defibrillator paddles 202*a* and 202*b*. It is formed from one or more sheet-like sections 610. The sheet-like sections 610 are connected in series. A flexible material extends between adjacent sheet-like sections 610 to form a crease line 608 that allows for folding along the crease line 608. The crease line 608 may involve any easily bendable structure. For example, the crease line 608 may be formed from a bendable, flexible material, such as a soft plastic, a mechanical joint, a hinge, etc. When the seal is broken and the defibrillator paddles 202*a* and 202*b* are pulled apart from one another, the connecting structure 206 unfolds, as shown in FIG. 6B.

The connecting structure 206 may take any appropriate form that is easily compressible and expandable. Some implementations involve coupling the connecting structure 106 with mechanisms that help compress it, expand it or address safety concerns. For example, one embodiment of the connecting structure 206 takes the form of a coilable ribbon. The ribbon is coiled within one or both of the defibrillator paddles 202*a* and 202*b* when the paddle module 104 is still sealed. When the defibrillator paddles 202*a* and 202*b* are pulled apart, the ribbon uncoils and extends substantially flat between the paddles. An additional benefit of the coiled ribbon may be reduced strain. That is, the reduction or elimination of folds and sharp bending in the ribbon may help reduce stress on the ribbon and any flex circuit or electrical connections inside the ribbon. In one embodiment, a recoiling mechanism within at least one of the paddles exerts a recoiling force on the ribbon, so that it tends to remain generally taut and flat between the paddles, even when the paddles are not pulled apart to their maximum extent. In still another embodiment, one or more of the defibrillator paddles 202*a* and 202*b* includes a spring or lever arranged to eject the connecting structure 206 out of the defibrillator paddle once the seal is broken and the paddle module 204 is opened. Some approaches involve a mechanism in one or more of the defibrillator paddles 202 and 202*b* that helps prevent recompression or refolding of the connecting structure 206 once it has already be unfolded or decompressed. Such features help confirm whether the device has already been opened or tampered with.

Figure 7:
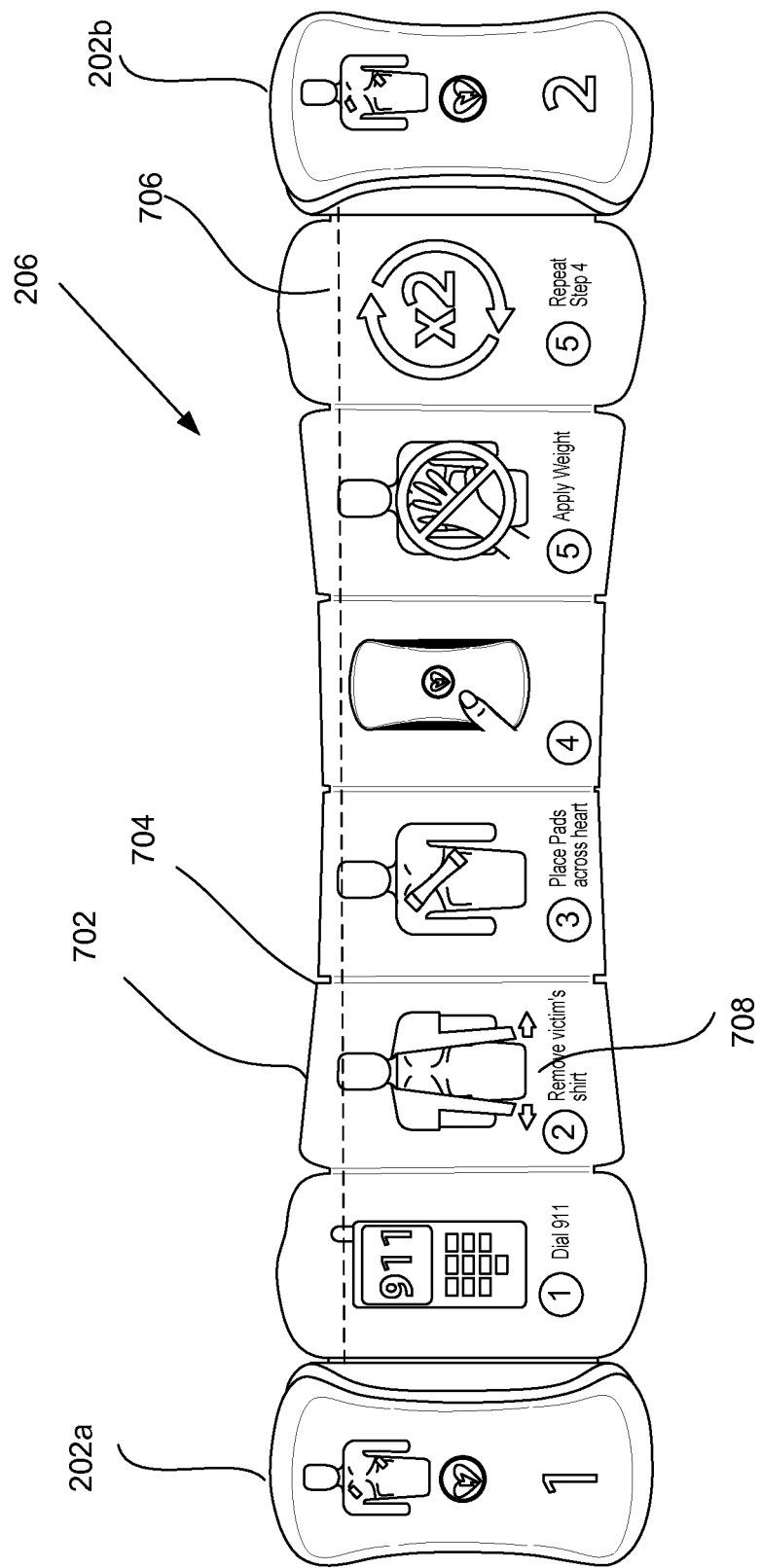
FIG. 7 illustrates a diagrammatic top view of a connecting structure that extends between two defibrillator paddles in accordance with a particular embodiment of the present invention.

Referring now to FIG. 7, the physical characteristics of one embodiment of a connecting structure 206 will be described in greater detail. The connecting structure 206 includes multiple sheet-like sections 702 that are arranged in series. In the illustrated embodiment, the connecting structure 206 forms a direct physical and electrical connection between the paddles, although other embodiments may include an intervening device and/or a power module. Adjacent sheet-like sections are foldable along crease lines 704. Embedded within the connecting structure 206 are one or more conductive wires 706, which serve to electrically couple the defibrillator paddles 202*a* and 202*b*.

The connecting structure 206 is formed from a electrically insulating material that covers the embedded conductive wires 706. When the paddles and the connecting structure 206 are positioned on the bare chest of a cardiac arrest victim and an electrical shock is delivered, a high voltage (e.g., between 1400 and 2000 volts) is generated between the defibrillator paddles. To minimize the undesirable leakage of current from the embedded wires 706 and help prevent a short circuit, the insulating material in the connecting structure 206 helps direct electrical current through the embedded conductive wires 706 rather than through the body of the victim. Therefore, all or substantially all electrical current that is applied to the body using the defibrillator is applied through the defibrillator electrodes.

The connecting structure 206 can also help instruct a user on the proper operation of the defibrillator. This information may be conveyed in a wide variety of ways. In the illustrated embodiment, for example, each sheet-like section 702 includes a surface 708 with instructions in the form of drawings. The drawings illustrate various steps in properly using the defibrillator. The instructions are not limited to drawings, however. In various embodiments, one or more of the sheet-like sections 702 may include a display screen, an audio speaker, a light-emitting diode, a light source etc. Such components are coupled with at least one of the paddles and a battery of the defibrillator via conductive wires in the connecting structure 206. Accordingly, instructions on using the defibrillator may be conveyed using computer graphics, audio, the selective flashing or coloration of lights, etc.

The connecting structure 206 of FIG. 7 is arranged to be easily viewable by a person using the defibrillator. In the illustrated embodiment, when the defibrillator paddles are pulled apart and the contact surfaces are facing in one direction (e.g., in the context of FIG. 7, into the page), the instructional surface 708 of the connecting structure 206 is arranged to generally face in the opposite direction (e.g., directly out of the page.) Therefore, the connecting structure 206, rather than merely helping to physically connect the defibrillator paddles 202a and 202b, can play a role in guiding the actions of a user while he or she is operating the defibrillator. As a result, there is less need for a separate instructional display elsewhere in the defibrillator, which in turn helps reduce the size and weight of the defibrillator as a whole.

Figure 8A:
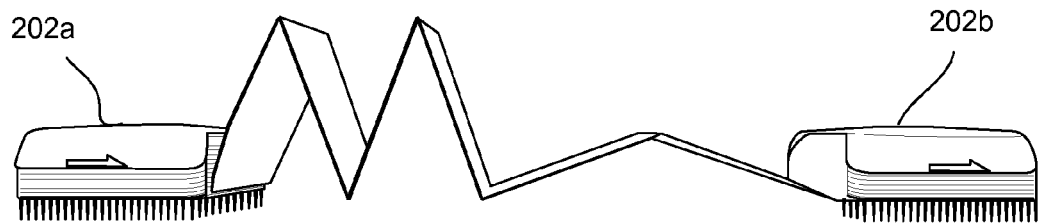
FIGS. 8A-8C diagrammatically illustrate defibrillators with paddles that each include electrically conductive protrusions in accordance with various embodiments of the present invention.
Figure 8B:
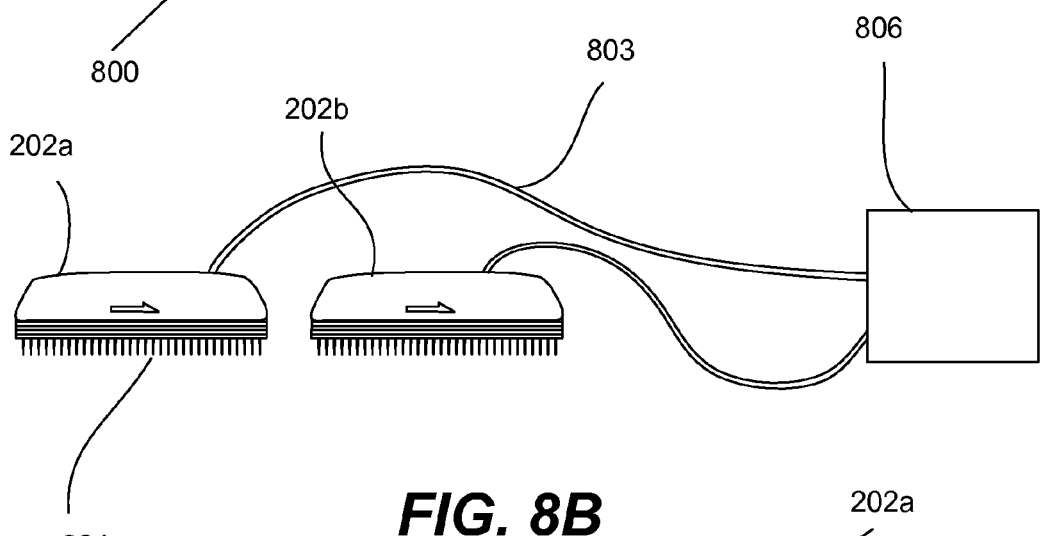

Referring now to FIG. 8A, a defibrillator 800 that uses conductive protrusions 804 will be described. In the illustrated embodiment, the conductive protrusions 804 extend out of each defibrillator paddle 202a and 202b. The conductive protrusions 804 are coupled with the electrical system of the defibrillator 800. The electrical system, which includes one or more batteries and capacitors, may be stored within one or more of the defibrillator paddles 202a and 202b, as shown in FIG. 8A, or in an external power module 806, as shown in FIG. 8B. In the latter case, the electrical system in the power module 806 is coupled with the conductive protrusions 804 in the paddles via one or more cables 803. The conductive protrusions 804 are part of the defibrillator electrode in each paddle and are arranged to optimize current flow through a sudden cardiac arrest victim.

Generally, the conductive protrusions 804 are arranged to press or penetrate into the skin of the victim. Such pressing or penetration reduces the electrical resistance of the skin. As a result, less voltage needs to be generated at the conductive protrusions 804 to ensure a current sufficient to arrest a cardiac arrhythmia in the victim. The corresponding reduction in power requirements for the defibrillator 800 may translate into a reduction in size of the electrical system of the defibrillator (e.g., a reduction in the size of its capacitors and/or batteries), which in turn helps enhance the portability of the defibrillator 800. In some embodiments, the volume of all capacitors in the defibrillator 800 may be limited to a total volume of approximately 400 cubic centimeters or less. In still other embodiments, the defibrillator 800 is arranged to apply a voltage at the defibrillator electrodes that is never in excess of 1400 volts during the normal operation of the defibrillator. (In comparison, some existing AEDs require the application of much more than 1400 volts to defibrillate a person.)

Figure 8C:
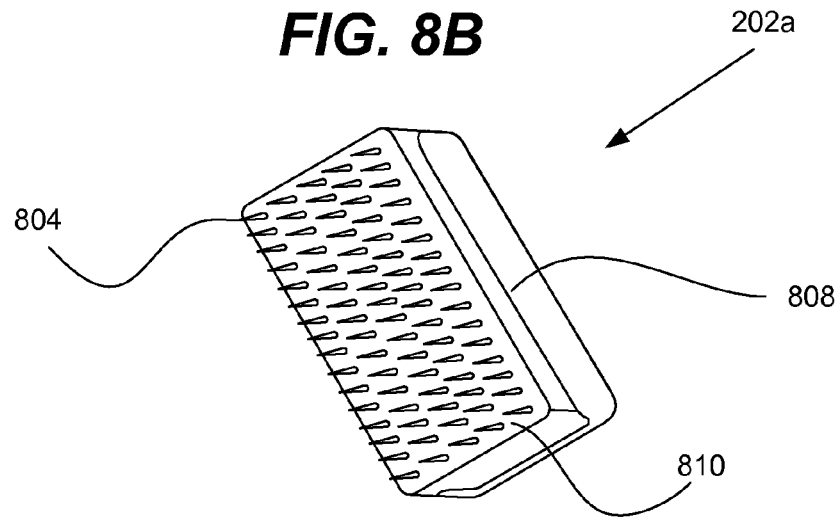

FIG. 8C illustrates an enlarged view of one of the defibrillator paddles 202a and its conductive protrusions 804 according to one embodiment of the present invention. The defibrillator electrode is coupled with the electrical system of the defibrillator (not shown) and includes an electrically conductive base plate 808. Extending substantially perpendicular out of a surface 810 of the base plate 808 are the conductive protrusions 804. During defibrillation, the contact surface 810 is arranged to face and be pushed into the skin of the victim, such that the contact protrusions 804 are embedded into the skin of the victim. It should be appreciated that the conductive protrusions 804 depicted in FIG. 8C are diagrammatic, are not drawn to scale and may have any suitable dimensions. By way of example, the protrusions may be tiny relative to the base plate 808 and/or almost invisible to the human eye.

The conductive protrusions may be arranged in any manner suitable for helping to minimize the electrical resistance in the outer layers of the skin. By way of example, the conductive protrusions 804 in FIG. 7C may be densely distributed across the contact surface 810 (e.g., at least 1 million protrusions or more on the surface 810) in a bristle-like arrangement. Some embodiments involve conductive protrusions 804 that are wire-like, pointed, tapered and/or sharp. In one implementation, at least a portion of each conductive protrusion 804 has a diameter of less than 33 gauge on the Stubs scale. In still other embodiments, the conductive protrusions 804 are not bristle- or needle-like, but instead may each have substantially broader bases and/or distinctly different forms from what is shown in FIGS. 8A-8C.

Where the conductive protrusions 804 are arranged to penetrate the skin of a person, proper sterilization may become a concern. Accordingly, in a preferred embodiment, pre-sterilized conductive protrusions 804 on defibrillator paddles 202a and 202b are initially sealed within a paddle module 204, as described previously in connection with FIGS. 1-6. To preserve the sterility of the protrusions 804, the paddle module 204 may be watertight and/or hermetically sealed. Some designs involve protrusions 804 that have a sterilization assurance level (SAL) of approximately $10^{-3}$ or less. Thus, when a user breaks the frangible seal of the paddle module 204, he or she can have greater confidence that the conductive protrusions 804 have not penetrated the skin of another person and are not contaminated. However, it should be appreciated that the described conductive protrusions 704 may be used in almost any known type of defibrillator system and are not limited to being used in the sealed paddle module 104 or any other previously described embodiment.

Figure 9A:
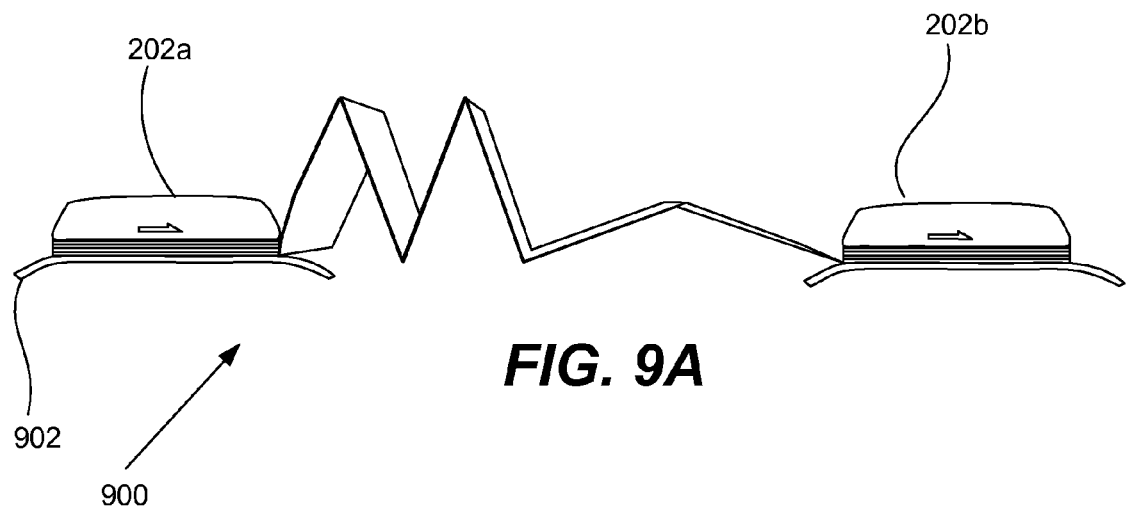
FIG. 9A-9B illustrate diagrammatic side and top views of a defibrillator with paddle guards in accordance with a particular embodiment of the present invention.

Referring next to FIG. 9A, an embodiment of a defibrillator 900 with paddle guards 902 will be described. The paddle guards 902 extend out from the bottom of each defibrillator paddle 202a and 202b and help protect the user's hands from contacting the body of the victim. Although generally not considered to be dangerous, contact with a victim during defibrillation may cause a small amount of electrical current to flow through the user of the defibrillator. The guards 902 can provide protection against electrical shock and also provide a degree of psychological comfort to the user who is operating the defibrillator. The paddle guards 902 may be integrated into the defibrillator paddles or patches of any suitable type of known defibrillator, including but not limited to any of the previously described embodiments.

Figure 9B:
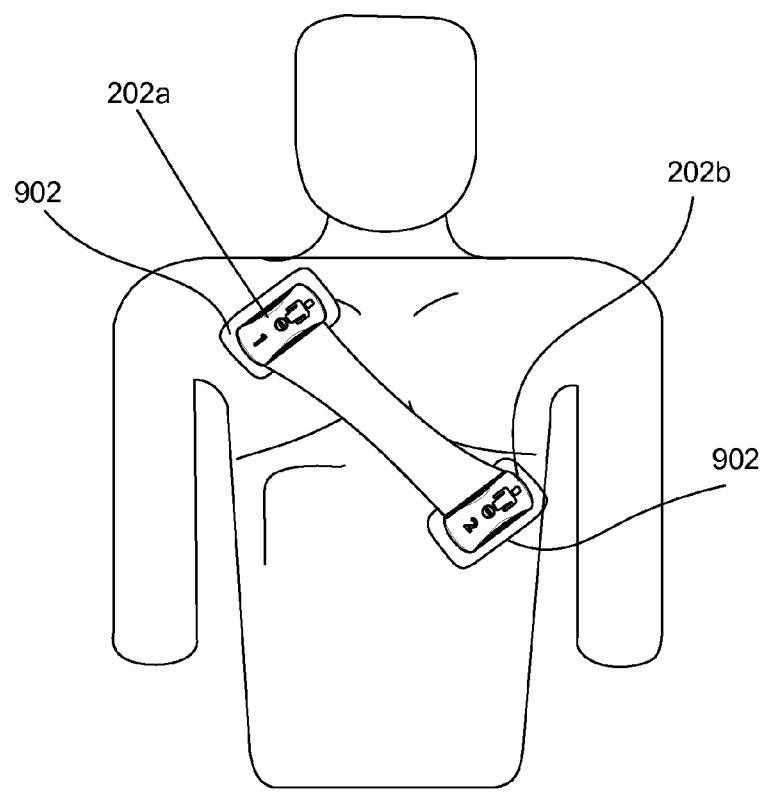

FIG. 9B illustrates a top view of defibrillator paddles 202a and 202b and their associated paddle guards 902 after the paddles have been positioned over the chest of a sudden cardiac arrest victim. In the illustrated embodiment, the paddle guard 902 extends substantially beyond the profile of its associated defibrillator paddle 202a. In some embodiments, the paddle guard extends approximately 1 cm or more from the housing of the defibrillator paddle 202a in a direction outward and parallel to a contact surface of the paddle. As a result, when a user puts his hands over the defibrillator paddles 202a, the paddle guard 202 is arranged to catch a finger or thumb that slips off of the paddle and would otherwise land onto the chest of the victim.

The paddle guards 902 may be deployed from the defibrillator paddles 202a and 202b in a wide variety of ways. In a preferred embodiment, the paddle guard 902 is specifically designed not to interfere with the contact area between the skin and the exposed electrically conductive area of its respective defibrillator paddle. In one embodiment, the defibrillator paddle 202a and 202b, each of which includes a compressed paddle guard 902, are sealed within a paddle module 204, as previously described in FIGS. 1-6. When sealed, the compressed paddle guards 902 do not extend beyond the profiles of their respective defibrillator paddles. For example, they may be folded directly between the sealed paddles 202a and 202b. When the paddle module 204 is opened, the paddle guards 902 expand out of the housing of the defibrillator paddles 202a and 202b to extend therefrom in the manner of FIGS. 9A and 9B. For such applications, the paddle guard 902 is preferably made from a flexible, electrically insulating material (e.g., plastic, etc) Some applications, however, contemplate a paddle guard 902 that is made of a stiffer material and/or that extends outside the housing of the associated defibrillator paddle 202a/202b, even while the defibrillator paddles 202a and 202b remain sealed as the paddle module 204.

Figure 10A:
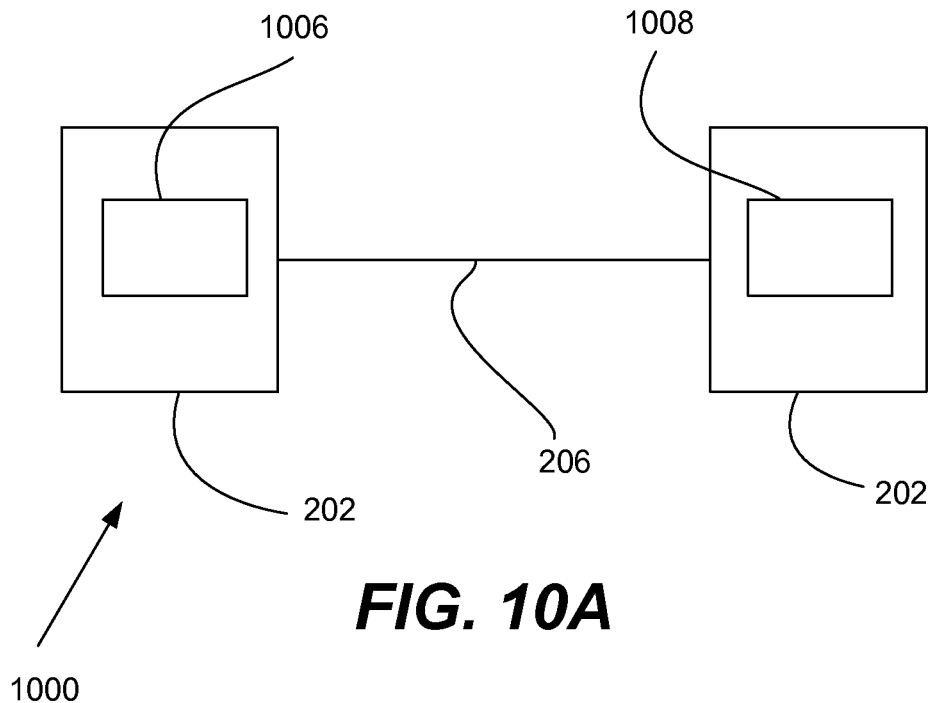
FIGS. 10A-10B are block diagrams indicating different arrangements of the defibrillator electrical system in accordance with various embodiments of the present invention.
Figure 10B:
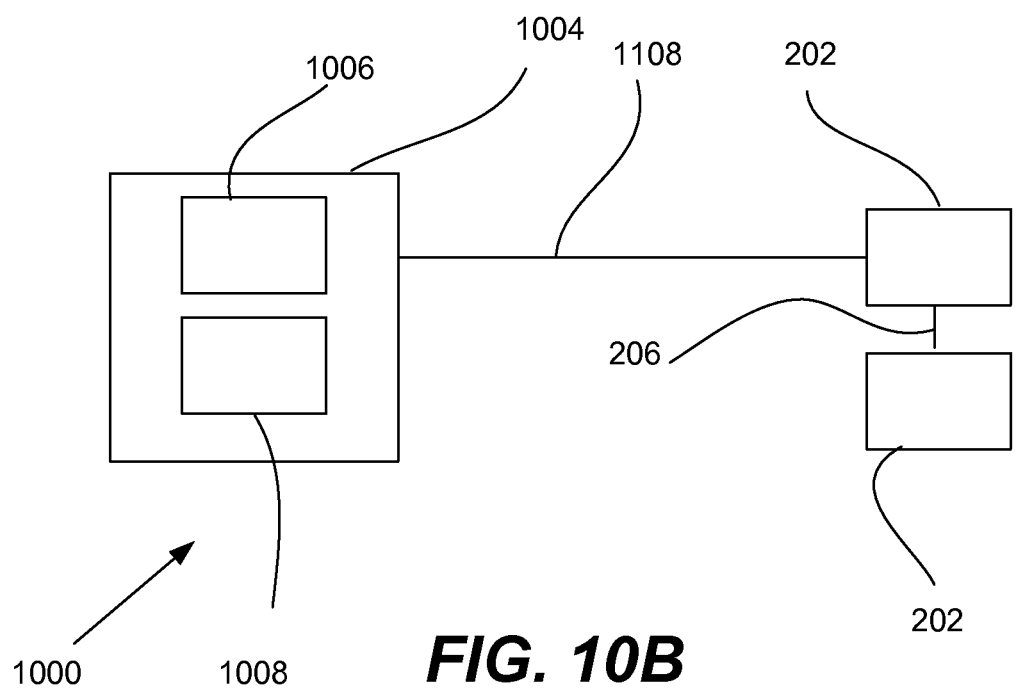

Referring now to FIGS. 10A and 10B, embodiments of defibrillators 1000 with different types of electrical systems will be described. In each figure, an electrical system including at least one capacitor 1006 and at least one battery 1008 is coupled to defibrillator electrodes in each paddle, although parts of the electrical system may be distributed within the defibrillator 1000 in different ways. Some designs involve positioning a capacitor 1006 and/or a battery 1008 within the housing of one or more of the defibrillator paddles 202. An example of this approach is presented in FIG. 10A, which illustrates an internal capacitor 1006 in the paddle 202a, an internal battery 1008 in the paddle 202b, and a connecting structure 206. The batteries and capacitors may be arranged among the defibrillator paddles in any suitable manner e.g., they may be divided among the paddles, all of the batteries and capacitors may be in just one paddle, etc. In some embodiments, any battery or capacitor that is electrically coupled with any of the defibrillator paddles 202 is situated only inside of the housing of the paddles. Another configuration is shown in FIG. 10B, where some or all of the capacitors and batteries of the defibrillator 1000 are situated within the housing of an external power module 1004. The external power module 1004 is coupled to one or more of the defibrillator paddles 202 with a cable 1108. In some implementations, as seen in FIG. 10B, the power module 1004 is directly connected to one of the paddles, while the paddles are directly connected to one another via connecting structure 206. In still other embodiments, the power module 1004 is connected directly and individually to the two paddles 202 with two separate cables 1108.

Figure 11A:
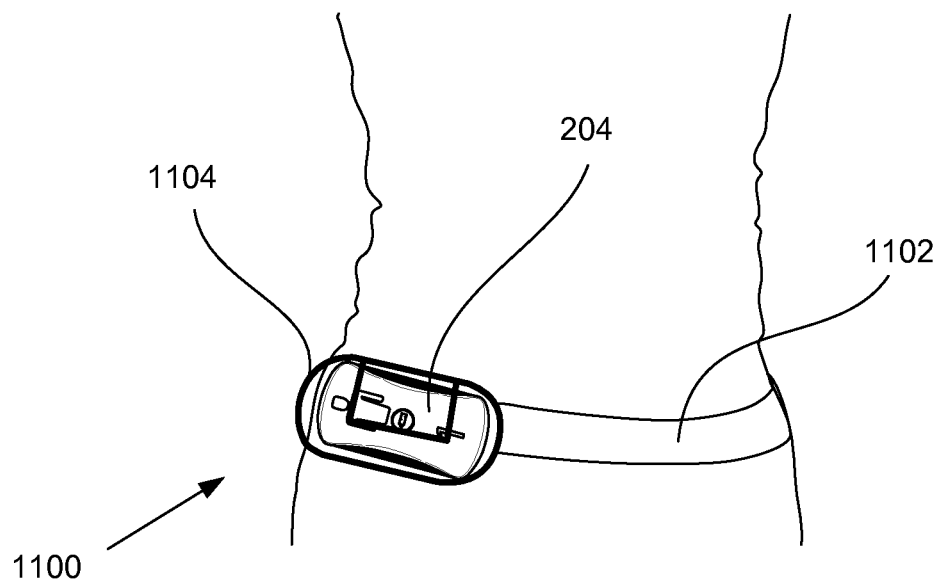
FIGS. 11A-11B diagrammatically illustrate a belt with an attached power module and paddle module in accordance with a particular embodiment of the present invention.

Referring next to FIG. 11A, an embodiment of a belt-mounted portable defibrillator 1100 will be described. The defibrillator 1100 includes a paddle module 204 and an external power module 1104, which are both attached to a belt 1102. The power module 1104 contains an electrical system for delivering electrical shocks through the paddles sealed in the paddle module 204. In this arrangement, the defibrillator 1100 has a power system external to the paddles, but nevertheless can be conveniently carried and rapidly deployed as necessary to defibrillate a victim of sudden cardiac arrest.

Figure 11B:
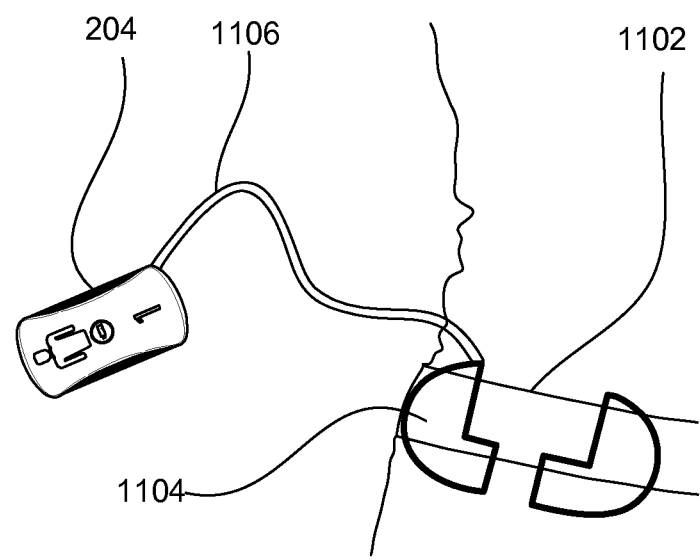

In various embodiments, a user wearing the defibrillator 1100 need not remove, activate or otherwise be distracted by the external power module 1104 to defibrillate someone. As shown in FIG. 11B, a user with a belt-holstered defibrillator 1100 may simply withdraw the paddle module 204 from the belt 1102, break the seal, and apply the defibrillator paddles as previously discussed. The external power module 1104 is coupled with and provides necessary power to the defibrillator paddles through the extendable cable 1106. Some implementations involve a cable 1106 that is coiled within the external power module 1104 or at the belt 1102 and that is increasingly uncoiled and exposed as the paddles of the paddle module 204 are positioned further away from the external power module 1104. In still other embodiments, the external power module 1104 is arranged to exert a pulling and/or recoiling force on the cable 1106 to help reduce unnecessary slack in the cable 1106. The power module 1104, the paddle module 204 and/or any associated container(s) may be secured to the belt 1102 using any suitable means, such as a latch, a hook, a clip, a locking mechanism, etc. It should be appreciated that various embodiments of the belt-mounted power module 1104 may be reused and/or recharged after the paddles have been used to defibrillate a person. That is, the belt-mounted defibrillator 1100 may be but is not necessarily limited to "one use," as the term is described herein with respect to various other defibrillator applications.

Figure 12A:
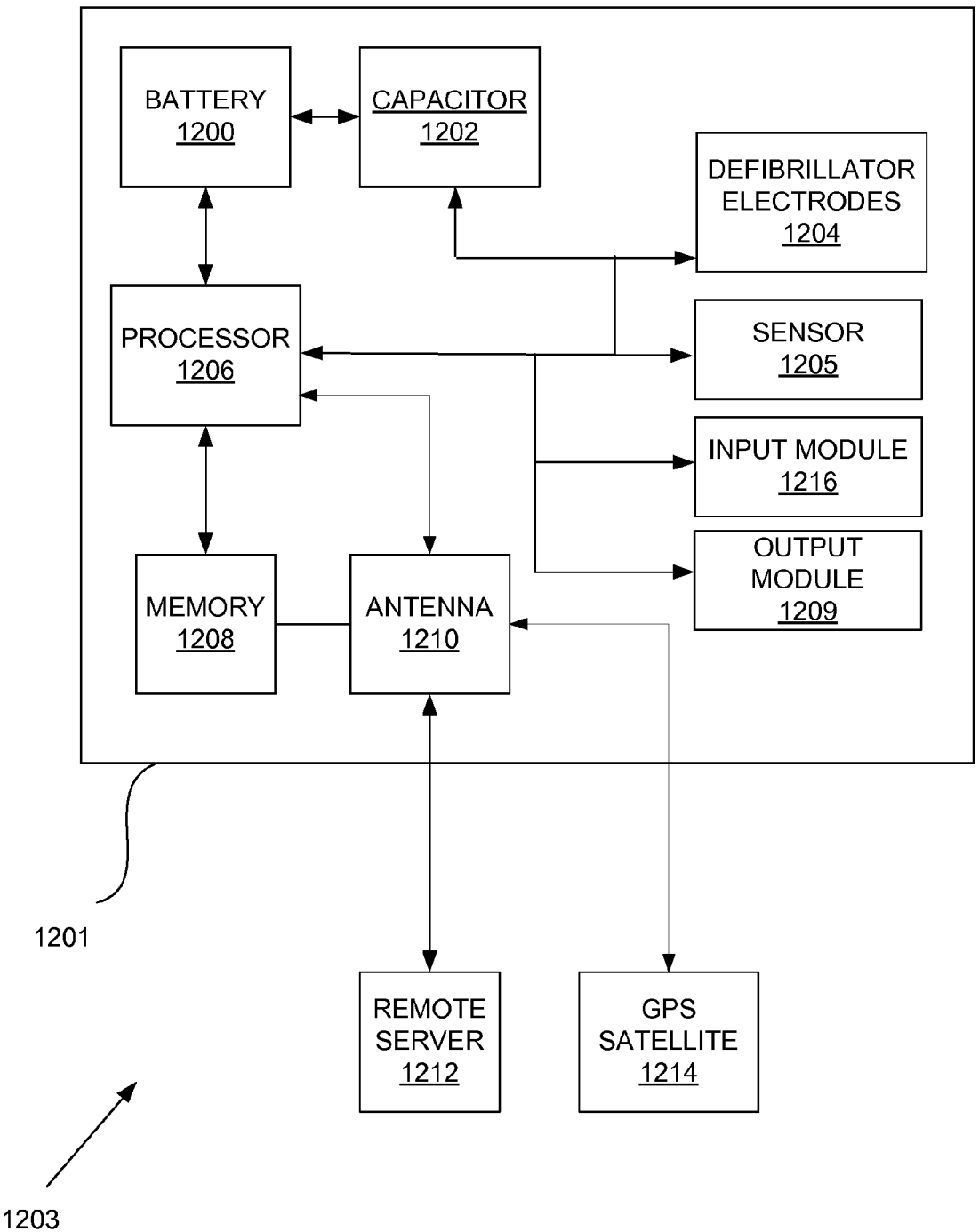
FIG. 12A is a block diagram illustrating various components of a defibrillator and associated devices in accordance with a particular embodiment of the present invention.

Referring next to FIG. 12A, a block diagram 1200 describing various components of an exemplary defibrillator 1201 is illustrated. In the illustrated embodiment, the defibrillator 1201 includes a battery 1200, capacitor 1202, defibrillator electrodes 1204, sensor 1205, processor 1206, input module 1216, output module 1209, memory 1208 and wireless antenna 1210. The wireless antenna 1210 is arranged to communicate with a wide variety of devices (e.g., a remote server 1212, an emergency services network and/or a GPS satellite 1214.) It should be appreciated that although the aforementioned components are referenced in the singular, the defibrillator 1002 may include one or more of each component as appropriate (e.g., multiple batteries, capacitors, etc.)

The battery 1200 may be coupled with and provide electrical power to all of the electrical components of the defibrillator 1201, including the processor 1206, the memory 1208, the antenna 1210, the defibrillator electrodes 1204 and the capacitor 1202. In preparation for defibrillation, battery 1200 is arranged to charge the capacitor 1202. Once charged and at the appropriate time, the capacitor 1202 is arranged to deliver an electrical shock via the defibrillator electrodes 1204.

When placed on the chest of a victim, the defibrillator electrodes 1204 receive electrical signals from the heart of the victim. These electrical signals are transmitted to the processor 1206. Computer code for processing the electrical signals may be stored in the memory 1208. The memory 1208 is suitable for storing a wide variety of computer readable data, including computer code for transmitting data, receiving data from, and controlling battery 1200, capacitor 1202, defibrillator electrodes 1204, sensor 1205, input module 1216, output module 1209, antenna 1210, remote server 1212 and GPS satellite 1214. The processor 1206 is arranged to execute any computer code stored in the memory 1208.

Output module 1209 relates to any electrical component suitable for conveying information to the user. Examples include a speaker, an LCD screen, an electronic ink display, a plasma screen, one or more light-emitting devices, etc. Any suitable exterior portion of the defibrillator 1201 may serve as a location for the output module 1209, e.g., the housing of one or both defibrillator paddles, the connecting structure, etc. Output module 1209 is coupled with the processor 1206 and may be arranged to respond to various signals received by the processor 1206. For example, when the processor 1206 determines that signals received through defibrillator electrodes 1204 correspond with a cardiac arrhythmia, this finding may be expressed to the user using the output module 1209 e.g., through the flashing of light, a line of electronic text, an audio prompt, etc.

Processor 1206 may also receive signals from the sensor 1205. Sensor 1205 includes any sensor suitable for assessing the physical environment around or within the defibrillator 1201. In some preferred embodiments, the sensor 1205 detects the breaking or opening of a frangible seal that helps secure the two defibrillator paddles 202a and 202b of FIGS. 1-6 to one another. When the processor 1206 receives this information, a variety of actions may be triggered. By way of example, the charging of the capacitor 1202 by the battery 1200 may be initiated. In some embodiments, a wireless message may be sent via the antenna 1210 to the remote server 1212. In still other embodiments, the processor 1208 will receive GPS data from GPS satellite 1214 via antenna 1210. Based on the GPS data, a wireless message indicating the global position of the defibrillator 1201 is then sent to the remote server 1212 and/or an emergency services network.

Some designs incorporate other types of sensors 1205, such as pressure or moisture sensors. In one embodiment, for example, a pressure sensor 1205 is coupled with a defibrillator electrode 1204 in one or both of the paddles. The pressure sensor 1205 may measure the amount of pressure being applied against the chest of a cardiac arrest victim. The processor 1206 receives this information and instructs output module 1209 to provide appropriate information to the user (e.g., a flashing light, text line and/or audio prompt indicating insufficient or sufficient pressure.) In still another embodiment, a moisture sensor 1205 coupled with the defibrillator electrode 1204 may measure the degree of moisture in the vicinity of the defibrillator electrodes. Particularly with respect to victims of swimming accidents, excessive moisture can sometimes obstruct the flow of defibrillation current through the heart of a person, thus rendering defibrillation ineffective. In such applications, the processor 1206 may assess signals from the moisture sensor 1205 and likewise convey appropriate instructions to the user via the output module 1209 (e.g., a flashing light, text line and/or audio prompt indicating the presence of too much water or sufficient dryness.) Various designs prevent the charging of the capacitor 1202 and/or the delivery of a shock at the defibrillator electrodes 1204 until the moisture sensor and/or the pressure sensor indicate that there is sufficient dryness and pressure, respectively.

Input module 1216 relates to any port arranged to receive input from an external source. By way of example, input module 1216 may be an infrared receiver, a USB port, a wireless receiver, etc. A keyboard, a laptop, external electronic module or other device may then be used to transmit data to the processor 1206 and the memory 1208 using the input module 1216. In some embodiments, a laptop, cell phone, a digital recorder or other electronic device may be used to transmit relevant customizable data e.g., name, cell phone number, address, emergency phone numbers, doctor's phone number, audio recordings, etc. to the processor 1206 via the input module 1216. Afterward, processor 1206 stores the data in the memory 1208. When the processor 1206 is alerted by the sensor 1205 that the seal has been opened and the defibrillator 1201 is about to be used, the processor 1206 may perform various actions based on the stored data. In one embodiment, the processor 1206 may then identify a destination device using the stored customizable data and establish a communications link e.g., the emergency line of a medical facility may be identified and called using a stored phone number, so that a stored, pre-recorded message may be transmitted to the staff there. In still another embodiment, personal customizable data is transmitted to a remote server 1212 at a medical facility to inform them that the defibrillator is about to be used. In another example, initiating the device and/or unsealing the defibrillator within a hospital setting may trigger a signal directing emergency personnel to the location of the device and/or the appropriate site or room. It should be appreciated that the defibrillator 1201 need not necessarily directly perform any of the above actions. Instead, when the seal is opened, the processor 1206 may send any stored data via antenna 1210 to a remote server 1212, and then help direct the remote server 1212 to make the desired calls and transmissions.

Antenna 1210 is arranged to communicate wirelessly with remote devices, such as a remote server 1212 or GPS satellite 1214. Remote server 1212 relates to one or more of any electrical device suitable for communicating with antenna 1210 (e.g., a network device, a cell phone, a computer, etc.) Antenna 1210 may represent multiple as opposed to just one physical antenna. For example, some embodiments include separate antennae for GPS and remote server access. Data may be transmitted using any suitable telecommunications or wireless protocol, including an Internet Protocol such as TCP. Since the need to use the defibrillator and to contact medical personnel may occur anywhere and possibly in very remote areas, antenna 1210 may be configured to exchange data with a variety of cellular networks, communications satellites and/or transmitters. That is, antenna 1210 is preferably capable of communicating with distant devices that are not near, physically connected to or within line-of-sight of the defibrillator 1201.

Figure 12B:
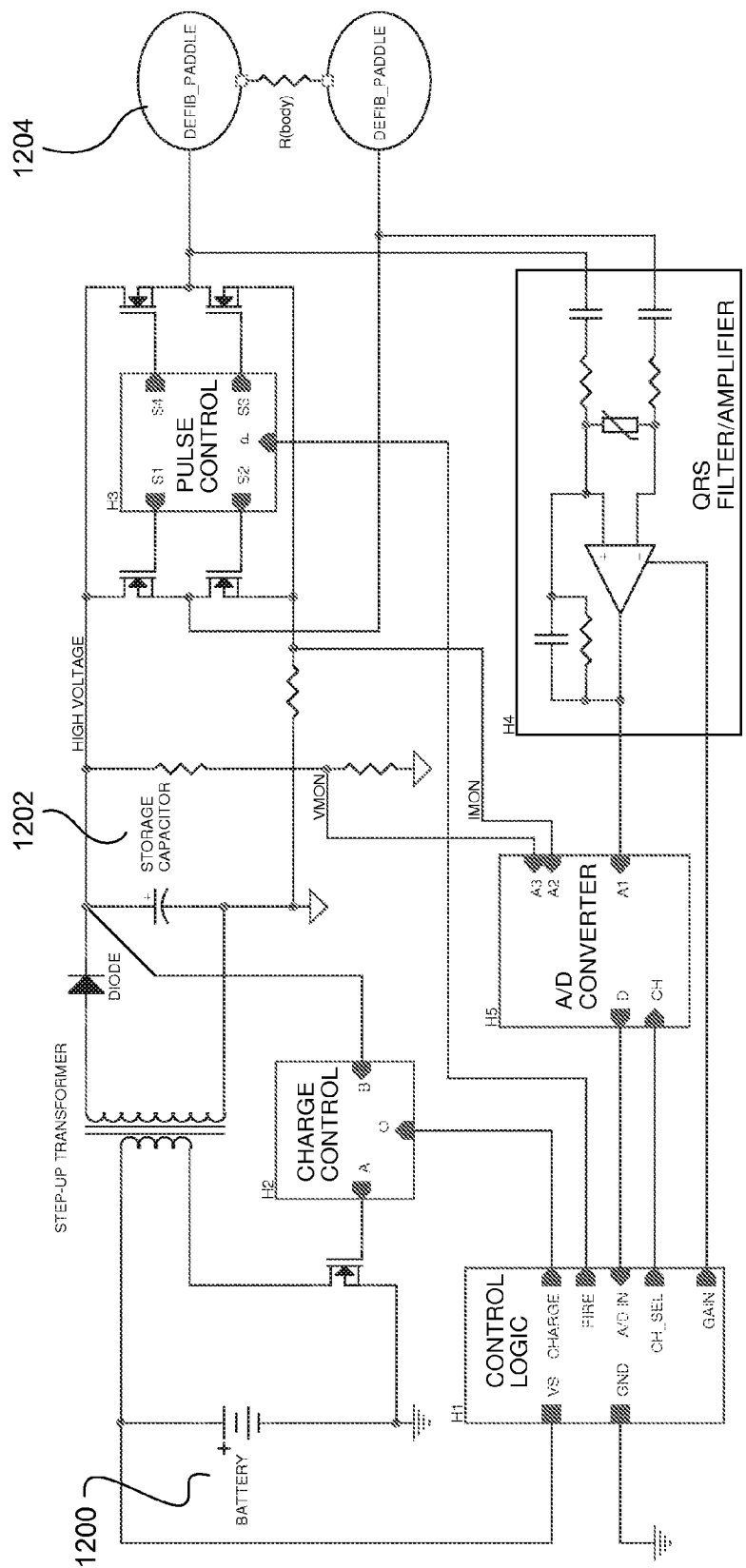
FIG. 12B is a circuit diagram for a defibrillator according to a particular embodiment of the present invention.
Figure 12C:
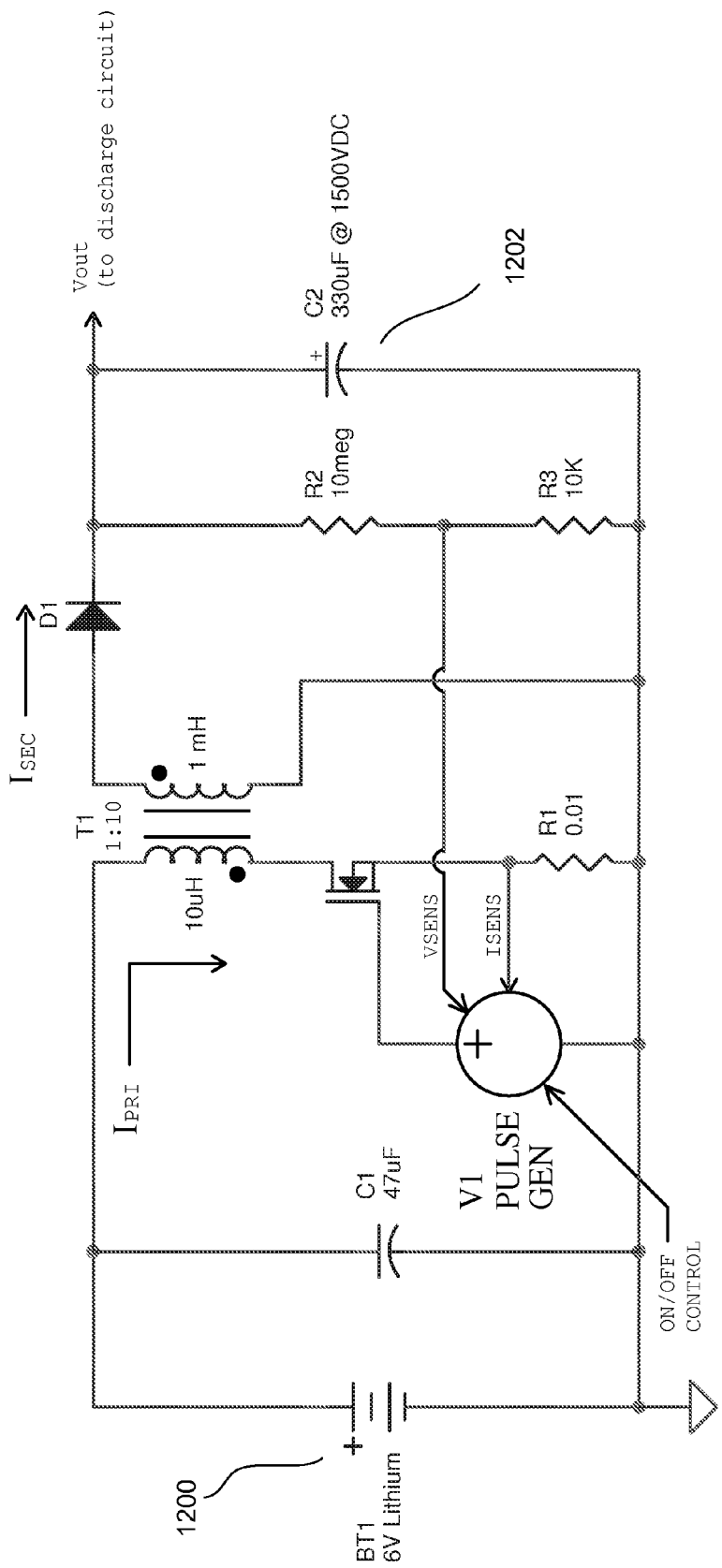
FIG. 12C is a circuit diagram for a charging circuit of a defibrillator according to a particular embodiment of the present invention.

Referring next to FIG. 12B and FIG. 12C, exemplary electrical designs for a defibrillator according to a particular embodiment of the present invention will be described. As will be appreciated by a person of ordinary skill in the art, FIG. 12B illustrates an exemplary circuit diagram that electrically couples a battery 1200, a capacitor 1202 and defibrillator electrodes 1204. FIG. 12C illustrates an exemplary charging circuit for charging the storage capacitor 1202 using the battery 1200. It should be noted that the component values and circuit arrangements depicted in FIGS. 12B and 12C relate only to particular embodiments and may be modified to suit the needs of particular applications.

Figure 13:
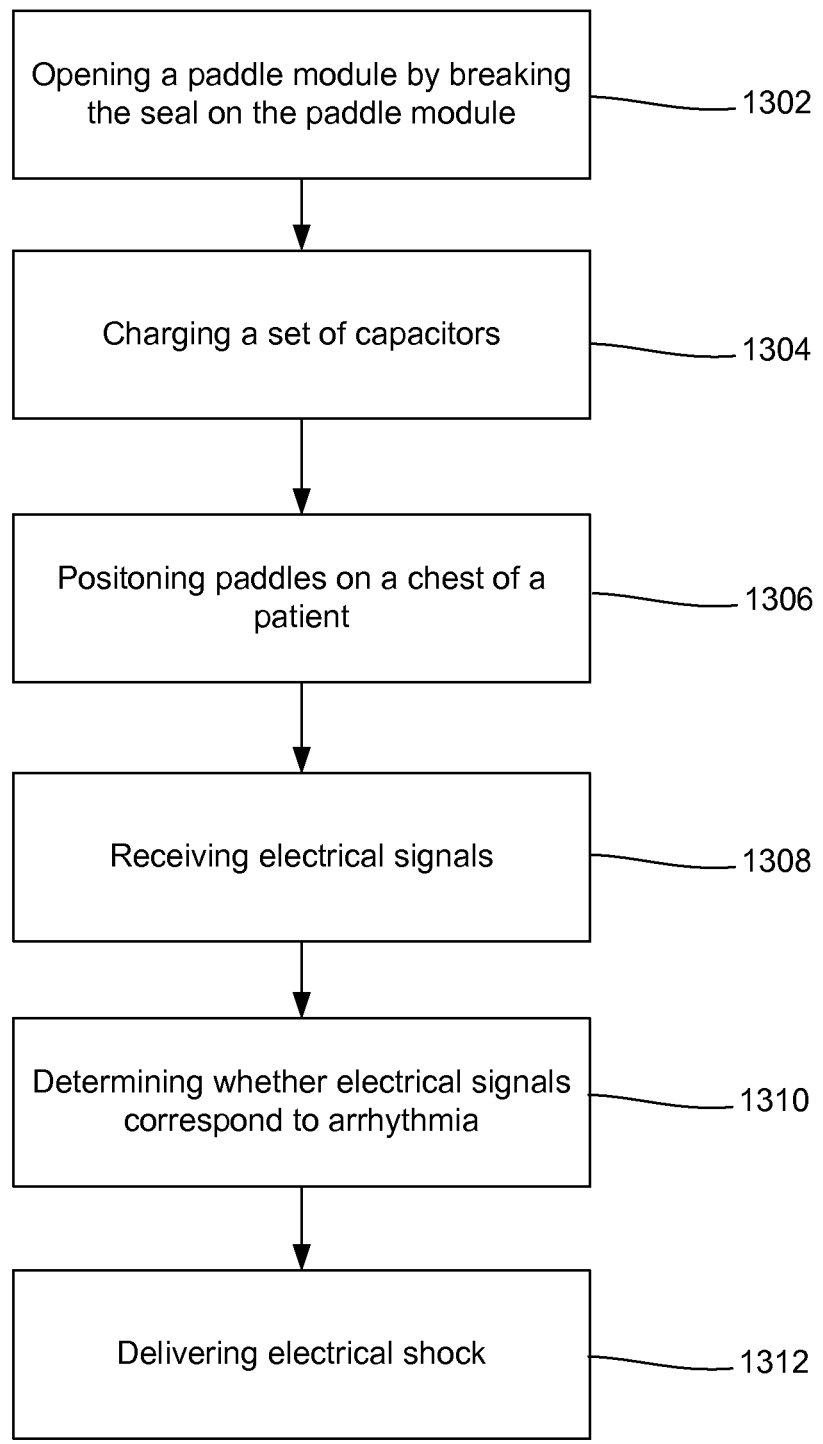
FIG. 13 is a flow chart illustrating a method of using a defibrillator in accordance with a particular embodiment of the present invention.
Figure 14A:
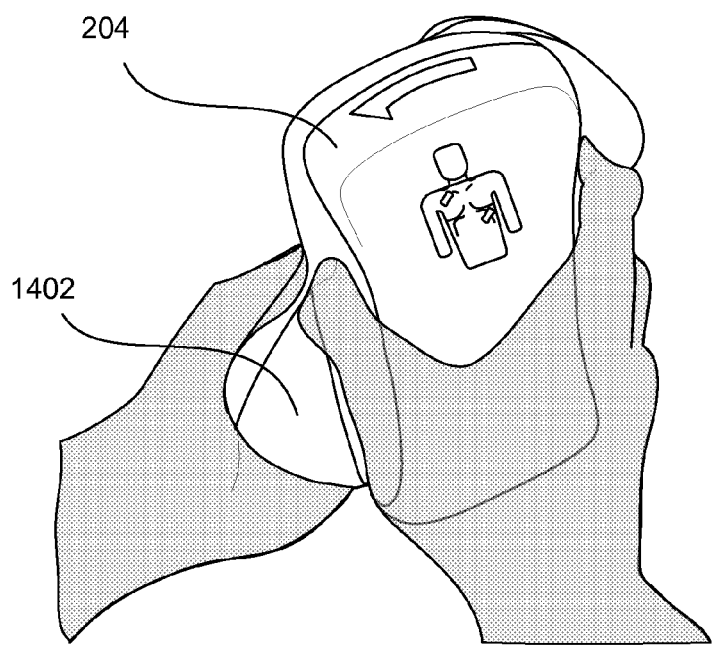
FIG. 14A illustrates a diagrammatic perspective view of a paddle module that is being unsealed in accordance with a particular embodiment of the present invention.
Figure 14B:
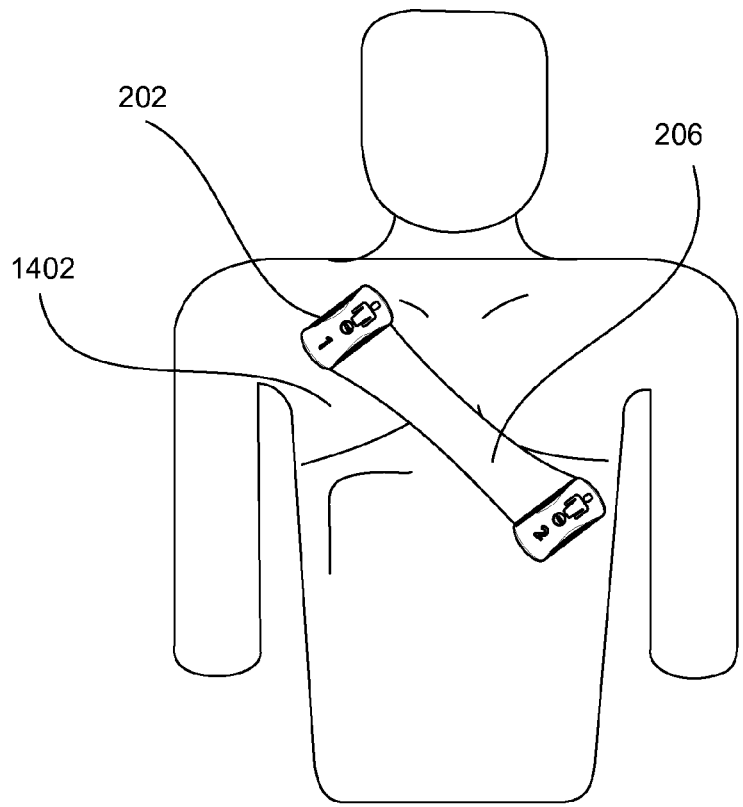
FIG. 14B illustrates a diagrammatic top view of a defibrillator being placed on a chest of a cardiac arrest victim in accordance with a particular embodiment of the present invention.
Figure 15:
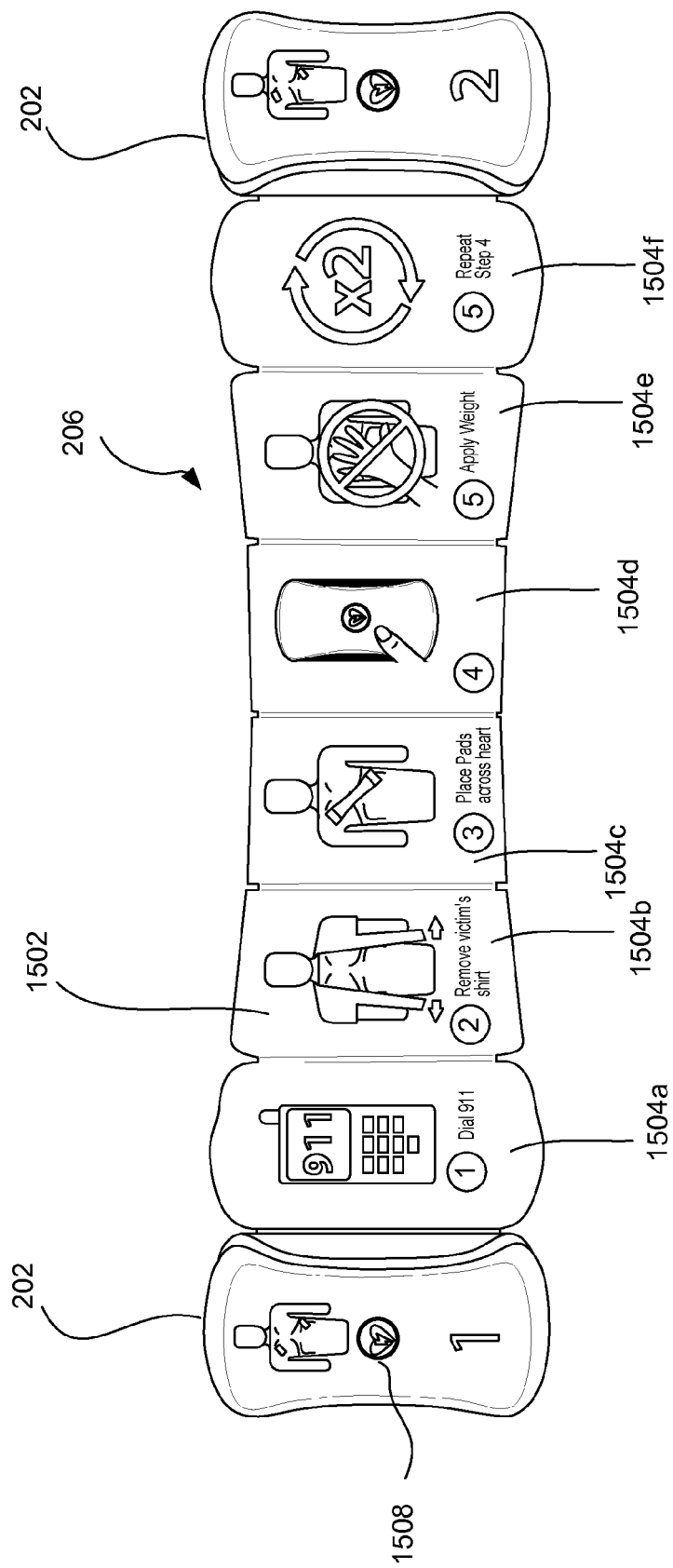
FIG. 15 illustrates a diagrammatic top view of a connecting structure that extends between two defibrillator paddles in accordance with a particular embodiment of the present invention.

Referring now to FIG. 13 and FIGS. 14-15, a method for using one of the aforementioned defibrillators according to an embodiment of the present invention will be described. Initially, the paddle module 204 of FIG. 14A is opened (step 1302). Preferably, the opening of the paddle module 204 involves the opening or breaking of a frangible seal, which can be detected by a sensor in the defibrillator and be used to trigger a wide variety of appropriate actions, as discussed earlier. Some designs involve the breaking of a pin or magnetic lock, the unfastening of a latch, the release of a locking mechanism, etc.

The opening of the paddle module 204 can be performed in a wide variety of ways. Preferably, the paddle module 204 is arranged in such a way such that the action required to open the paddle module 204 is clearly purposeful rather than accidental. In the illustrated embodiment, for example, a twisting motion is utilized to break the frangible seal. That is, the paddles are twisted in a direction substantially parallel to electrically conductive contact surfaces 1402 on the paddles. Various designs contemplate a wide variety of opening operations, including permanently deforming or physically tearing the seal, releasing a latch, breaking a magnetic lock, etc.

At some point after the opening of the seal, the one or more capacitors in the defibrillator will be charged by one or more batteries (step 1304.) As described earlier, the opening of the seal may trigger the charging of the capacitor. By way of example, a sensor may detect when the seal has been opened. Afterward, an opening confirmation signal may be transmitted by the sensor to a processor in the defibrillator. When the opening confirmation signal is received by the processor, the processor will respond by issuing a command to charge the capacitor. Accordingly, no additional manual intervention (e.g., the pressing of a button, the activation of a switch, the issuing of a command, etc.) by the user may be required to charge the capacitor once the seal has been broken or opened. Although some designs contemplate manual charging of the capacitor by the operator pressing a button, in some embodiments the capacitor is charged automatically upon the opening of the seal, so that the user has one less task to distract him or her.

A host of other actions may be triggered by the opening of the seal. By way of example, the sending of a wireless communication may be triggered based on the opening of the seal. That is, the processor in the defibrillator, after receiving an opening confirmation signal from a sensor that monitors whether the seal has been broken, automatically arranges for the transmission of a text message, phone call, email, etc. This automatic feature allows a user of the defibrillator to focus less on contacting third parties and more on monitoring the condition of the cardiac arrest victim.

After the opening of the paddle module 204, the defibrillator paddles 202 are pulled apart from one another and placed on the chest 1402 of the victim. (step 1306 and FIG. 14B). In a preferred embodiment, as discussed earlier, when the defibrillator paddles 202 are pulled apart, a connecting structure 206 is exposed from within the paddle module 204 and expands between the defibrillator paddles 202. The connecting structure 206 includes one or more sheet-like sections with a first and an opposing second surface. The first surface includes instructions for operating the defibrillator. When the defibrillator paddles 202 are positioned properly on the chest 1402 of the victim (i.e., such that exposed portions of the connecting structure 206 are flat and not twisted and electrically conductive contact surfaces of the defibrillator paddles 202 are positioned apart and face in a downward direction towards the chest 1402), the first surface of the connecting structure 206 faces upward towards the user. Accordingly, a user holding the paddles can easily review the instructions on the first surface of the connecting structure 206 simply by looking downward.

Once the defibrillator paddles 202 are placed appropriately, defibrillator electrodes within each paddle begin receiving electrical signals from the heart of the victim (step 1308). The electrical signals are received by a processor in the defibrillator. The processor determines whether the electrical signals correspond to a cardiac arrhythmia (step 1310).

When a cardiac arrhythmia is found, one or more charged capacitors within the defibrillator may release their charge through the defibrillator electrodes in the paddles. The release of electrical charge results in the delivery of an electrical shock (step 1312). The electrical shock may take any form suitable for arresting a cardiac arrhythmia. In a preferred implementation, if no cardiac arrhythmia is detected that would be conducive to a defibrillation (step 1310), the defibrillator would remain in a monitoring mode, charged and ready to deliver a shock (step 1312) should the victim's rhythm deteriorate. By way of example, the shock may involve a monophasic or biphasic discharge between approximately 150 and 250 joules, a voltage of approximately 1400 to 2000 volts at the defibrillator electrodes and/or last between 4 and 20 milliseconds. In some embodiments, the shock is only delivered manually (e.g., after the user activates a button, lever or switch to trigger the shock.) Some designs involve automatic delivery of the shock. That is, the shock is automatically delivered after a predetermined period of time as long as the defibrillator electrodes are still receiving electrical signals that correspond with a cardiac arrhythmia. In some designs, the user therefore need not depress a switch or perform additional actions to initiate the shock.

Some implementations restrict the number of shocks that may be delivered, in part to minimize the size of the electrical system of the defibrillator. To the best knowledge of the inventors, conventional automated external defibrillators are arranged to deliver numerous electrical shocks sufficient to arrest cardiac arrhythmia in multiple people without replacement of the defibrillator capacitors. Although such approaches have obvious advantages, it is believed that trading off longevity for portability may be advantageous in some applications. Also, users will be forced to return and refurbish used defibrillators, which encourages regular maintenance and may enhance their reliability and safety. Therefore, in some implementations, the memory in the defibrillator includes computer code for limiting the total number of electrical shocks given to the maximum number that may be expected to deliver an effective voltage for defibrillation. By way of example, the total number of electrical shocks may be limited to a designated number of shocks that is no more than approximately 4 to 10 shocks, even when electrical signals corresponding to a cardiac arrhythmia are still being received at the defibrillator electrodes. In still other implementations, all of the batteries in the defibrillator are collectively sized and rated to generate no more than the designated number of shocks at the electrodes without any recharging.

For a person without medical or professional training, carrying out the above operations can be stressful, particularly in a life-or-death situation involving the defibrillation of a cardiac arrest victim. Accordingly, it is helpful to provide easy-to-use instructions with the defibrillator to assist the user in performing the above tasks. As discussed earlier, various designs involve a connecting structure 206, which includes multiple sheet-like sections with information for operating the defibrillator. Referring now to FIG. 15, a method for instructing a user in the operation of a defibrillator using the connecting structure 206 will be described. FIG. 15 includes defibrillator paddles 202 and a connecting structure 206 that physically and electrically couples them together. The connecting structure 206 includes a segmented series of sheet-like portions 1502. Each sheet-like portion 1502 includes an instructional surface 1504*a*-1504*f* that is coupled to an electronic display device. Each electronic display device includes one or more lighting components of any suitable type (e.g., a light emitting device, a light reflecting device, an LED, a liquid crystal display, an electronic ink display, a computer display, a light source, etc)

The electronic display devices may change their flashing speeds, colors, sequencing, etc. to help guide a user through various operations involving the defibrillator. By way of example, each instructional surface 1504*a*-1504*f* may represent a particular operation in a sequence of operations for using the defibrillator. In the illustrated embodiment, instructional surface 1504*c* corresponds to the placing of the defibrillator paddles 202 on the chest of a person and the receiving of electrical signals therefrom. Therefore, when no electrical signals are being received at the defibrillator paddles 202, the electronic display device at the instructional surface 1504c may flash using a first sequence and/or a first color. In addition or alternatively, the device may display an image, symbol and/or message. When electrical signals are being received and are being processed, the electronic display device at the instructional surface 1504c may flash using a second sequence and/or a second color. When the electrical signals are being received and correspond with a cardiac arrhythmia, the instructional surface 1504c may flash using a third sequence and/or a third color. The first, second and third sequences and colors are different and thus can be used to distinguish between different modes of operation and/or results. To use a simple example, the first sequence (i.e., the one relating to not getting any electrical signals at the paddles at all) may be a slow flashing sequence and involve the color yellow. The second sequence (i.e., the one relating to getting and processing electrical signals at the paddles) may be a somewhat faster flashing sequence and involve the color green. The third sequence (i.e., the one relating to detecting a cardiac arrhythmia) may be a non-flashing, steady light held for a predetermined period and involve the color red. After the third sequence and color have been presented, paddle button 1508 and/or another instructional surface may light up, to indicate that an electrical shock will be delivered automatically and imminently, or to encourage the user to initiate an electrical shock manually (e.g., by pressing paddle button 1508). The aforementioned approach is but one technique among many for using flashing sequences, lighting, colors and other visual effects with the connecting structure 206 to guide a defibrillator user.

Figure 16A:
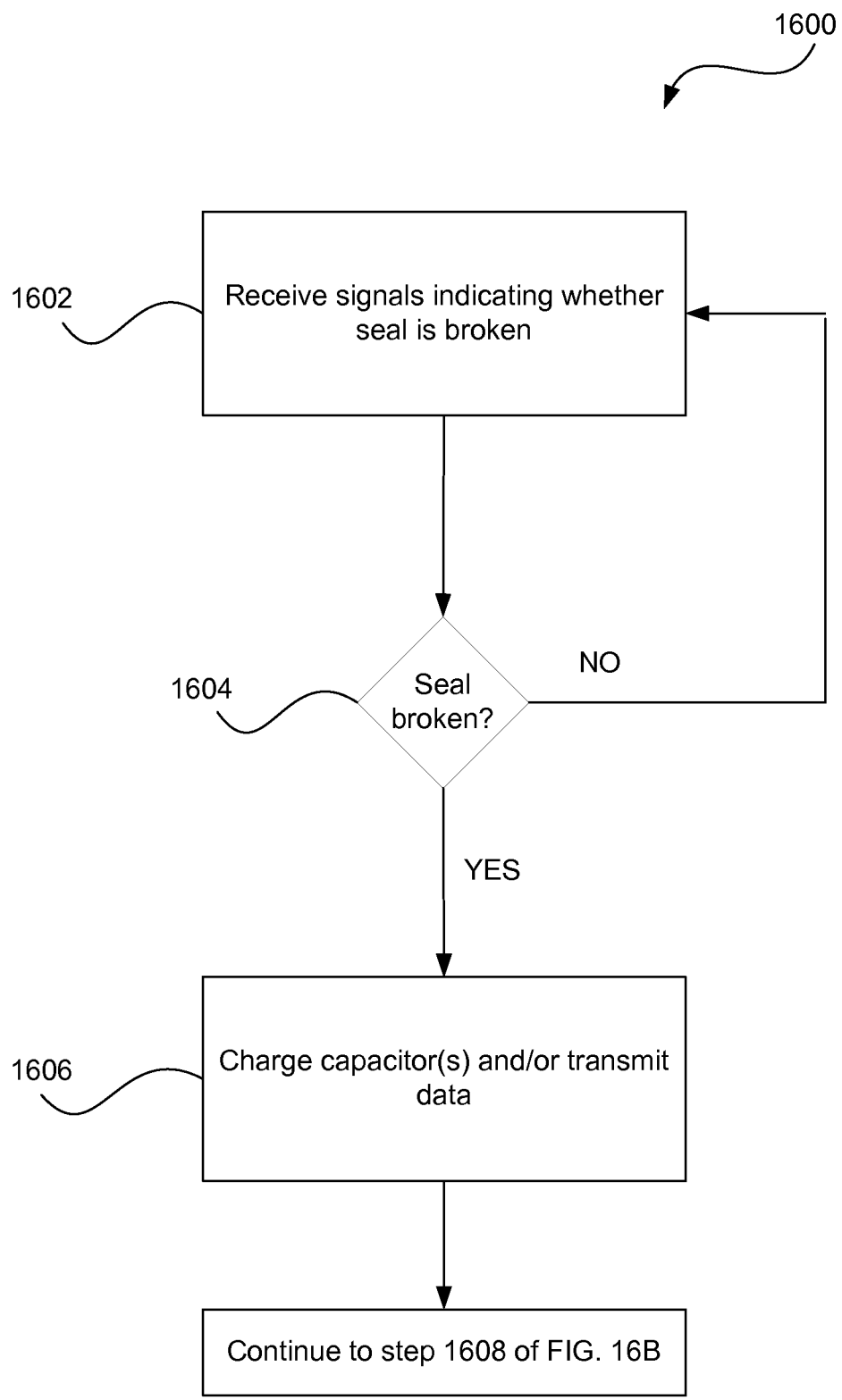
FIG. 16A is a flow diagram illustrating a method for automatically performing one or more actions based on the breaking of the defibrillator seal in accordance with a particular embodiment of the present invention.
Figure 16B:
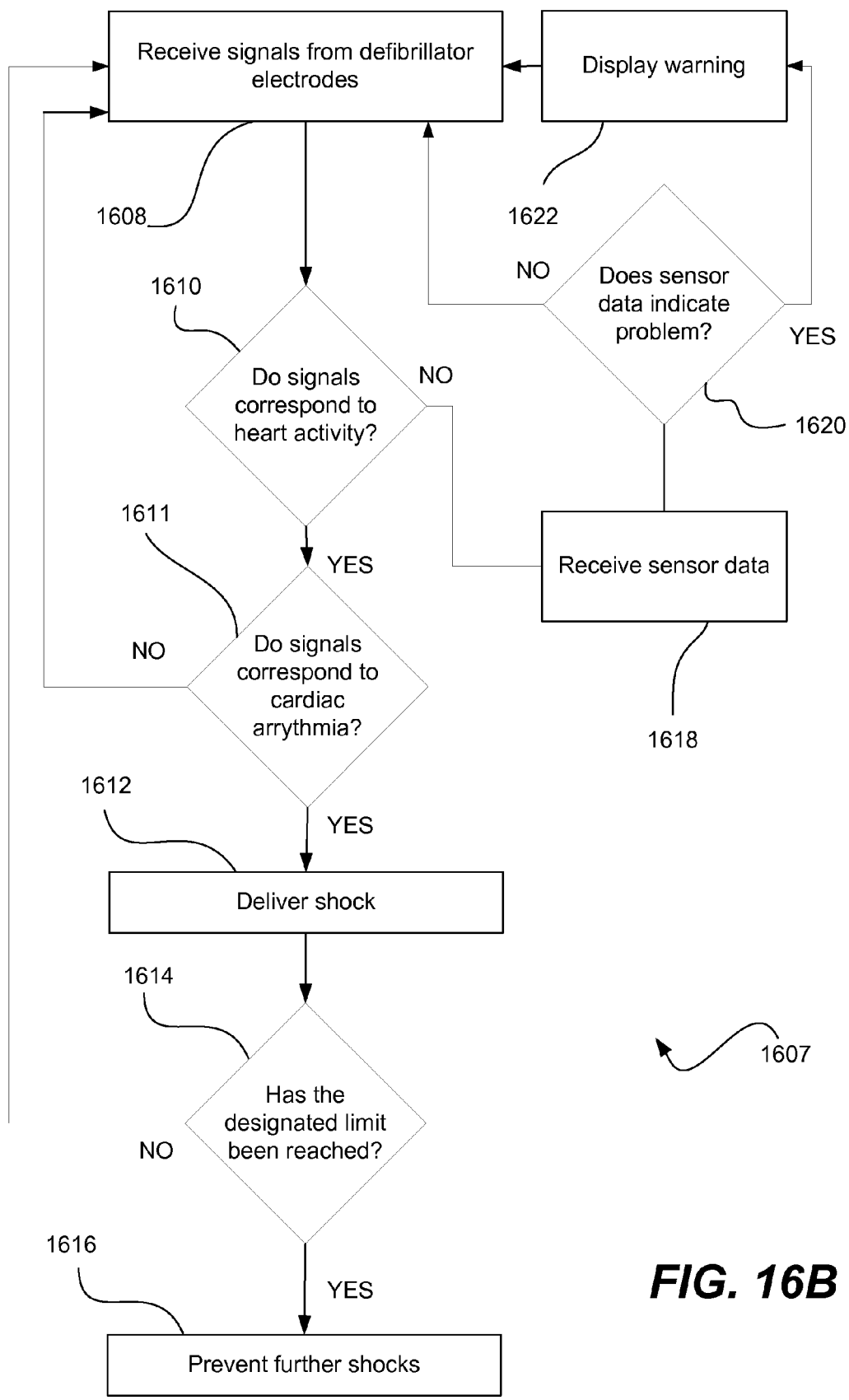
FIG. 16B is a flow diagram illustrating a method for performing one or more actions based on signals received from defibrillator electrodes in accordance with a particular embodiment of the present invention.

Referring now to FIGS. 16A and 16B, a method 1600 for operating a defibrillator according to one embodiment of the present invention is described. The steps of the method 1600 may be applied to any of the previously described defibrillator embodiments e.g., defibrillator 200 of FIG. 2A. Initially, in step 1602 of FIG. 16A, signals are received indicating whether a seal on the defibrillator has been broken. To conserve power, some embodiments involve a processor that is initially deactivated or in a low-power mode prior to the opening of the seal. The processor is then activated or powered in response to the opening of the seal without executing any computer code. In some implementations, the signals referenced in step 1602 refer to signals received by a defibrillator processor from a sensor that is coupled with the seal. As indicated in step 1604, the signals may be repeatedly checked to determine if the seal has been broken. If the seal has not been broken, time is allowed to pass and additional signals are received and analyzed. If the seal has been broken, one or more actions may be triggered. For example, a battery in the defibrillator may automatically charge a capacitor so that an electrical shock may be delivered at the defibrillator electrodes. Additionally or alternatively, data may be wirelessly transmitted. This has a wide variety of applications. By way of example, the transmitted data may take the form of an email sent to an email server, a text message sent to a cell phone, or data packets sent via an Internet protocol to a remote server. The data may include any relevant information e.g., the identity of the owner of the defibrillator, the current, GPS-derived location of the defibrillator, the cell phone number of the owner, etc. It should be appreciated that the operations of step 1606 are performed automatically upon a determination that the seal has been broken (step 1604) and do not require additional intervention by the user of the defibrillator (e.g., such actions do not require the pressing of a button, the manual activation of a switch, additional human interaction with the defibrillator, etc.)

Afterward, the method may optionally proceed to step 1608 of FIG. 16B. FIG. 16B describes a method 1607 for analyzing signals received from the defibrillator electrodes and limiting the number of electrical shocks that are applied at the defibrillator electrodes. At step 1608, signals are received from the defibrillator electrodes. The signals are analyzed to determine if they correspond to heart activity of any kind. For example, if the defibrillator paddles have not been placed on the chest or have been placed at the wrong locations, then the signals received through the defibrillator electrodes may be faint, erroneous or non-existent. Excessive moisture or inadequate pressure may also contribute to poor or distorted signals. In such cases, steps may be taken to improve the reception of the heart signals. For example, sensor data may be received from one or more sensors coupled with the defibrillator electrodes (step 1618). As discussed earlier in connection with FIG. 12A, a wide variety of sensors may be used, including pressure sensors, humidity/moisture sensors, etc. The sensors may help identify a reason for the erroneous, faint or non-existent signals e.g., inadequate pressure being applied to the defibrillator paddles, too much moisture on the chest of the person, improper positioning of the paddles, etc.) If such problems are detected, a suitable warning or message is displayed to help a user rectify the problem (steps 1620 and 1622). This warning or message may be conveyed to a user using a wide variety of mediums, including digital images, audio messages, electronic text on a display, lighting sequences, etc. Afterward, signals are again received at the defibrillator electrodes (step 1608) and the process of analyzing the signals begins again. Ideally, the warning message and sensor data will have helped the user to take corrective action and improve the signals received through the defibrillator electrodes.

If it is determined that the signals have adequate strength and clarity and correspond to some form of heart activity, whether abnormal or normal, the signals are then analyzed to see if they correspond to a cardiac arrhythmia (step 1611). If the signals reflect the normal functioning of the heart, an electrical shock is not delivered at that time. In a preferred embodiment, the defibrillator then remains in a monitoring or standby mode (i.e., the defibrillator electrodes again receives electrical signals at block 1608 and proceeds to block 1610.) In some implementations, when signals correspond with the normal functioning of the heart and/or the received heart signals match a particular predetermined pattern, further shocks may be prevented (step 1616). If the received signals correspond to a cardiac arrhythmia, then an electrical shock is delivered (step 1612). The total number of electrical shocks delivered using the method of FIG. 16B is counted (e.g., COUNT_SHOCKS=COUNT_SHOCKS+1, where COUNT_SHOCKS initially equals 0). At step 1614, the total number of delivered shocks is evaluated and compared against a designated, predetermined limit. For example, as described earlier in the application, the total number of allowable shocks may be limited to 4 to 10 shocks (e.g., LIMIT=5). If the limit has been reached (e.g., if COUNT_SHOCKS=LIMIT), then the delivery of any additional shocks may be prevented (step 1616). If the limit has not been reached, then the method returns to step 1611, where signals from the defibrillator electrodes are again assessed to determine if the shock managed to arrest the cardiac arrhythmia.

Although only a few embodiments of the invention have been described in detail, it should be appreciated that the invention may be implemented in many other forms without departing from the spirit or scope of the invention. For example, the present application refers to the term "shock" or "electrical shock." Generally, any reference in the present application to an "electrical shock" or "shock" may be understood as an electrical shock that is generated at the defibrillator electrodes, where each electrical shock lasts between 4 and 20 milliseconds, involves discharges of approximately 150 to 250 joules and/or involves applying a voltage at the defibrillator electrodes of between 1400 and 2000 volts. The electrical shock may involve any appropriate waveform known to a person of ordinary skill in the art e.g., biphasic, monophasic, etc. It should be appreciated, however, that for various applications electrical shocks with different electrical characteristics may be used (e.g., the voltage differential may be as high as 5000 volts, the discharges may be smaller than 150 joules or larger than 250 joules, etc.) Additionally, the features described in one of the described embodiments may be combined with or used to modify the features of almost any other described embodiment in the present application. For example, FIGS. 1-6 illustrate various defibrillators, most of which involve both a sealed paddle module 204 and connecting structure 206 with one or more sheet-like portions. Also contemplated by the present invention, however, is a sealed paddle module 204 without the connecting structure 206 and an unsealed defibrillator with the connecting structure 206. Similarly, the paddle guards 902 of FIG. 9B and the conductive protrusions 804 of FIG. 8C may be used on paddles or pads in almost any type of defibrillator arrangement, including but not limited to the sealed paddle module 204 and the connecting structure 206 of FIGS. 1-6. In another example, any of the steps of the methods depicted in FIGS. 16A and 16B may be combined with, modified based on or supplemented with features described in connection with FIG. 12A. Although the illustrated embodiments primarily depict defibrillator paddles with housings, in some applications pads rather paddles may be used. Generally, pads are understood as being thinner and more flexible than paddles. It should be appreciated, however, that any of the features attributed to the defibrillator paddles in the present application may instead be applied to defibrillator pads. Therefore, the present embodiments should be considered as illustrative and not restrictive and the invention is not limited to the details given herein, but may be modified within the scope and equivalents of the appended claims.

What is claimed is:

1. A portable defibrillator comprising:
two paddles electrically connected to each other, each paddle including a defibrillator electrode covered in a separate protective housing, the two paddles sealed together using a releasable seal to form a paddle module, the protective housings of the two paddles forming the exterior of the paddle module; and
an electrical system, incorporated partially within the paddle module, coupled to the defibrillator electrode in each paddle, the electrical system including at least a battery and a capacitor, the battery arranged to charge the capacitor, the capacitor arranged to apply a voltage at the defibrillator electrodes to facilitate delivering an electrical shock suitable for arresting a cardiac arrhythmia.

2. The portable defibrillator as recited in claim 1, wherein the releasable seal is frangible.

3. The portable defibrillator as recited in claim 1, wherein the releasable seal is formed using at least one selected from the group consisting of: a lock, a tape, an adhesive, a pin and a water resistant seal.

4. The portable defibrillator as recited in claim 1, further comprising a connecting structure between the two paddles including a sheet-like section having a first surface and an opposing second surface, the first surface of the connecting structure having instructions for using the defibrillator.

5. The portable defibrillator as recited in claim 4, wherein each defibrillator electrode includes a contact surface and wherein the paddles and the connecting structure are arranged such that the first surface of the connecting structure faces in a direction substantially opposite that of the contact surfaces of the paddles when the connecting structure is substantially fully extended and arranged substantially flat between the paddles.

6. The portable defibrillator as recited in claim 5, wherein the connecting structure includes at least one electrically conductive wire and a plurality of sheets made at least partly of an electrically insulating material, the at least one wire forming an electrical connection between the paddles and being embedded within at least one of the sheets, the plurality of sheets being flexibly and serially connected to form the connecting structure.

7. The portable defibrillator as recited in claim 4, wherein a display screen is mounted on the first surface of the connecting structure, the display screen electrically coupled to the electrical system and arranged to display instructions for using the defibrillator, the display screen being at least one selected from the group consisting of: an electronic display, an electronic ink display, a liquid crystal display, a plasma screen and a plurality of light emitting diodes.

8. The portable defibrillator as recited in claim 1, further comprising:
one or more processors coupled to the two paddles; and
a computer readable storage medium coupled to the two paddles and the one or more processors, the computer readable medium including computer code that is executable by the one or more processors, the computer code comprising:
executable computer code operable to assess whether the releasable seal has been broken;
executable computer code operable to charge the capacitor using the battery based on assessing whether the releasable seal has been broken; and
executable computer code operable to receive and analyze signals received from a chest of a person through the paddles.

9. The portable defibrillator as recited in claim 8, wherein the computer code further comprises:
executable computer code operable to determine whether the signals received from the chest of the person correspond to a cardiac arrhythmia; and
executable computer code operable to prevent a delivery of more than 10 electrical shocks by the paddles even when it is determined that the signals received from the chest of the person correspond to a cardiac arrhythmia.

10. The portable defibrillator as recited in claim 9, wherein the computer code further comprises:
executable computer code operable to send message data wirelessly to a remote server based on the assessing as to whether the releasable seal has been broken.

11. The portable defibrillator as recited in claim 10 wherein the message data includes at least one selected from the group consisting of: GPS data indicating a current location of the defibrillator and health data based on the signals received from the chest of the person.

12. The portable defibrillator as recited in claim 10, wherein the computer code further comprises:
executable computer code operable to receive and store customizable data from a computing device external to the defibrillator; and executable computer code operable to selectively identify a destination device based on the customizable data, wherein the message data is sent to the remote server identified using the customizable data.

13. The portable defibrillator as recited in claim 8 wherein:
at least one of the paddles includes a sensor;
the computer code further comprises executable computer code operable to receive and process sensor data from the sensor, the sensor data indicating at least one of the group consisting of: an amount of pressure applied against the paddle and an amount of moisture near the paddle; and
executable computer code operable to display a warning signal on an exterior of the defibrillator, the warning signal based on the received sensor data.

14. The portable defibrillator as recited in claim 1 wherein each paddle includes a paddle guard made of a flexible, electrically insulating material that is unexposed and disposed within the paddle module, the paddle guard arranged such that portions of a chest of the person outside a profile of each paddle are covered by the paddle guard when the paddle is placed on the chest of the person, thereby reducing a probability that an operator of the paddles will come in direct contact with the person receiving the therapeutic shock during defibrillation.

15. The portable defibrillator as recited in claim 1 wherein:
a total volume of the capacitor in the defibrillator is less than 600 cubic centimeters; and
the electrical system delivers less than 6 electrical shocks, each electrical shock lasting between 4 and 20 milliseconds and involving applying an electrical voltage of between 1400 and 2000 volts at the defibrillator electrodes.

16. The portable defibrillator as recited in claim 1 wherein each of the defibrillator electrodes is covered with an electrically conductive adhesive layer.

17. The portable defibrillator as recited in claim 1 wherein the exterior of the paddle module lacks sharp edges and is substantially smooth such that there is no recess anywhere on the exterior of the paddle module that is deeper than 4 millimeters, thereby reducing a tendency of the paddle module to get caught on other objects.

18. The portable defibrillator as recited in claim 1, wherein exposed portions of the housings of the paddles constitute at least a majority of all exposed surface area on the exterior of the paddle module.

19. The portable defibrillator as recited in claim 1 wherein the paddle module further comprises a ribbed membrane extending along a side of the paddle module to facilitate holding of the paddle module.

20. The portable defibrillator as recited in claim 1, wherein the paddles in the paddle module are arranged such that an electrically conductive contact surface on the two paddles directly face one another.

21. The portable defibrillator as recited in claim 1, wherein a display screen is mounted in the housing of one of the paddles, the display screen facing in a direction opposite that of the defibrillator electrode of the one of the paddles, the display screen electrically coupled to the electrical system to display images related to using the defibrillator.

22. The portable defibrillator as recited in claim 1, further comprising a power module that includes a housing, the electrical system being disposed at least in part within the housing of the power module, the power module being electrically and physically connected to at least one of the paddles via at least one cable.

23. The portable defibrillator as recited in claim 1, wherein each paddle includes a groove extending along a side arranged to receive a thumb of a person, the groove having a raised edge, the raised edge of each of the paddles cooperating to form a central ridge that extends along a central axis of the paddle module, the grooves of the sealed paddles being arranged symmetrically around the central ridge.

24. The portable defibrillator as recited in claim 1, wherein the electrical system generates no more than 10 shocks at the defibrillator electrodes of the paddles without a recharging of the battery.

25. The portable defibrillator of claim 1, wherein the electrical system is housed in one of the paddles.

26. The portable defibrillator of claim 1, wherein the electrical system is housed within the two paddles.

27. The portable defibrillator of claim 1, wherein the electrical system is partially housed within a separate power module.

28. The portable defibrillator of claim 1, wherein each defibrillator electrode includes a plurality of electrically conductive protrusions.

29. A portable defibrillator comprising:
two paddles, each paddle including a defibrillator electrode covered in a protective housing;
a connecting structure that electrically and physically connects the two paddles to each other;
an electrical system including at least a battery and a capacitor, the battery arranged to charge the capacitor, the capacitor arranged to apply a voltage at the defibrillator electrodes to facilitate delivering an electrical shock suitable for arresting a cardiac arrhythmia, a part of the electrical system being disposed within the housing of each paddle; and wherein the two paddles are sealed together using a releasable seal to form a paddle module such that the defibrillator electrodes of the paddles are unexposed and the housings of the paddles cooperate to form an exterior of the paddle module.

30. The portable defibrillator as recited in claim 29, wherein the releasable seal is frangible.

31. The portable defibrillator as recited in claim 30, wherein the releasable seal involves at least one selected from the group consisting of: a tape, an adhesive, a water resistant seal and a pin.

32. The portable defibrillator as recited in claim 29, wherein:
the connecting structure is folded and positioned directly between the defibrillator electrodes of the two paddles; and
the connecting structure is arranged to unfold when the two paddles are unsealed and pulled away from one another.

33. The portable defibrillator as recited in claim 29, wherein;
each paddle in the paddle module includes a recess, the recesses of the paddles cooperating to form a cavity in the paddle module; and
the connecting structure is positioned within the cavity.

34. The portable defibrillator of claim 29, wherein each defibrillator electrode includes a plurality of electrically conductive protrusions.

35. A portable defibrillator comprising:
two paddles, each paddle including a defibrillator electrode covered in a protective housing;
a connecting structure that electrically and physically connects the two paddles to each other;
an electrical system including at least a battery and a capacitor, the battery arranged to charge the capacitor, the capacitor arranged to apply a voltage at the defibrillator electrodes to facilitate delivering an electrical shock suitable for arresting a cardiac arrhythmia, a part of the electrical system being disposed within the housing of each paddle; and wherein the connecting structure includes a sheet-like section with a first surface and an opposing second surface, the first surface of the connecting structure having instructions on using the defibrillator, the paddles and the sheet being arranged such that the first surface of the connecting structure faces in a direction substantially opposite that of a conductive surface of the paddles when the connecting structure is substantially fully extended and arranged substantially flat between the paddles.

36. A portable defibrillator comprising:

two paddles, each paddle including a defibrillator electrode covered by a protective housing;

a flexible connecting structure that physically and electrically connects the two paddles to each other, the connecting structure having a sheet-like section with a first surface and an opposing second surface, the first surface of the connecting structure displaying instructions for using the defibrillator; and an electrical system coupled with the two paddles, the electrical system including at least a battery and a capacitor, the battery arranged to charge the capacitor, the capacitor arranged to apply a voltage at the defibrillator electrodes to facilitate delivering an electrical shock suitable for arresting a cardiac arrhythmia.

37. The portable defibrillator as recited in claim 36 wherein the connecting structure includes a plurality of serially connected sheet-like sections, the connecting structure being foldable along crease lines dividing the sheet-like sections, adjacent sheet-like sections being connected to one another using at least one of the group consisting of: a hinge, a binding and a plastic material.

38. The portable defibrillator as recited in claim 36 wherein the paddles and the connecting structure are arranged such that the first surface of the connecting structure faces in a direction substantially opposite that of contact surfaces of the defibrillator electrodes when the connecting structure is substantially fully extended and arranged substantially flat between the paddles.

39. The portable defibrillator as recited in claim 36, wherein the two paddles are sealed together using a releasable seal to form a paddle module such that the defibrillator electrodes of the paddles are unexposed and the housings of the two paddles cooperate to form the exterior of the paddle module.

40. The portable defibrillator as recited in claim 39 wherein the paddle module includes one or more springs coupled with the connecting structure, the one or more springs arranged to apply pressure upon the connecting structure, such that the connecting structure springs out from the paddles when the releasable seal of the paddle module is opened and the paddles are moved apart from one another.

41. The portable defibrillator as recited in claim 39, wherein:

the connecting structure is folded and positioned directly between the defibrillator electrodes of the two paddles; and the connecting structure is arranged to unfold when the two paddles are unsealed and pulled away from one another.

42. The portable defibrillator as recited in claim 39, wherein:

the connecting structure is coiled within the paddle module; and the connecting structure is arranged to uncoil when the two paddles are unsealed and pulled away from one another.

43. The portable defibrillator as recited in claim 36, wherein the connecting structure includes one or more embedded conductive wires that are covered in an electrically insulating material, the insulating material in the connecting structure helping to limit the leakage of current from the wires and direct electrical current through the connecting structure, such that electrical current is applied to a body of a person entirely through the defibrillator electrodes when the defibrillator electrodes have a voltage differential of between 1400 and 2000 volts and the defibrillator electrodes and the connecting structure are positioned on the body of the person.

44. The portable defibrillator of claim 36, wherein each defibrillator electrode includes a plurality of electrically conductive protrusions.

* * * * *